(12) United States Patent
Shah

(10) Patent No.: US 10,451,641 B2
(45) Date of Patent: Oct. 22, 2019

(54) COMPOSITIONS AND METHODS FOR METABOLIC PROFILING IN SUBJECTS WITH HEART FAILURE WITH PRESERVED EJECTION FRACTION

(71) Applicant: Duke University, Durham, NC (US)

(72) Inventor: Svati Shah, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/557,621

(22) PCT Filed: Mar. 14, 2016

(86) PCT No.: PCT/US2016/022388
§ 371 (c)(1),
(2) Date: Jan. 26, 2018

(87) PCT Pub. No.: WO2016/149220
PCT Pub. Date: Sep. 22, 2016

(65) Prior Publication Data
US 2018/0067137 A1 Mar. 8, 2018

Related U.S. Application Data

(60) Provisional application No. 62/132,848, filed on Mar. 13, 2015.

(51) Int. Cl.
*G01N 33/92* (2006.01)
*G01N 33/50* (2006.01)
(Continued)

(52) U.S. Cl.
CPC ............... *G01N 33/92* (2013.01); *A61B 5/00* (2013.01); *A61B 5/4842* (2013.01); *G01N 33/50* (2013.01);
(Continued)

(58) Field of Classification Search
CPC ........ A61B 5/00; A61B 5/4842; G01N 33/64; G01N 33/6812; G01N 33/6893;
(Continued)

(56) References Cited

U.S. PATENT DOCUMENTS

2005/0106104 A1  5/2005 Rosenberg
2007/0077548 A1  4/2007 Boger
(Continued)

FOREIGN PATENT DOCUMENTS

WO  WO 2007/103124  9/2007
WO  WO 2009/014639  1/2009

OTHER PUBLICATIONS

Shah et al. (Circulation., 2012; 126(9): 1110-1120) (Year: 2012).*
(Continued)

*Primary Examiner* — Jeremy C Flinders
(74) *Attorney, Agent, or Firm* — Michael Best & Friedrich LLP

(57) ABSTRACT

Disclosed herein are compositions and methods for targeted metabolomics profiling to provide absolute quantification of a broad array of metabolic intermediates of fatty acids, amino acids, and carbohydrate metabolism for HFpEF. In an aspect, the disclosure relates to a method for assessing risk of death or a major adverse cardiac event (MACE) in a subject diagnosed with heart failure with preserved ejection fraction (HFpEF). The method may include (a) determining in a sample from the subject the level of each metabolite in at least one factor, wherein the factor is selected from the group consisting of factor 1, factor 3, factor 4, factor 5, factor 10, factor 12, and factor 14; and (b) comparing the level of each metabolite in the sample to a standard, wherein the level of the metabolite in the subject relative to a standard is indicative of the risk of death or MACE in the subject.

17 Claims, 3 Drawing Sheets

(51) Int. Cl.
  *G01N 33/64* (2006.01)
  *A61B 5/00* (2006.01)
  *G01N 33/68* (2006.01)
  *A61B 5/1468* (2006.01)

(52) U.S. Cl.
  CPC ......... *G01N 33/64* (2013.01); *G01N 33/6812* (2013.01); *G01N 33/6893* (2013.01); *A61B 5/1468* (2013.01); *G01N 2560/00* (2013.01); *G01N 2570/00* (2013.01); *G01N 2800/325* (2013.01); *G01N 2800/52* (2013.01); *G01N 2800/56* (2013.01)

(58) Field of Classification Search
  CPC ............... G01N 33/92; G01N 2560/00; G01N 2570/00; G01N 2800/325; G01N 2800/52; G01N 2800/56; G01N 33/00
  See application file for complete search history.

(56) References Cited

U.S. PATENT DOCUMENTS

2008/0073500 A1   3/2008  Cerda
2011/0318726 A1*  12/2011 Shah .................. A61B 5/00
                                            435/4

OTHER PUBLICATIONS

Heather et al. (Journal of Molecular and Cellular Cardiology, 2013, 55:2-11) (Year: 2013).*
Aguer C et al. "Acylcarnitines: potential implications for skeletal muscle insulin resistance," FASEB, Journal. 2015, 336-345.
Almasy et al., "Multipoint Quantitative-Trait Linkage Analysis in General Pedigrees," Am J Hum Genet, 1998, vol. 62, pp. 1198-1211.
An et al., "Hepatic expression of malonyl-CoA decarboxylase reverses muscle, liver and whole-animal insulin resistance," Nat Med, 2004, vol. 10, No. 3, pp. 268-274.
Beekman et al., "Heritabilities of apolipoprotein and lipid levels in three countries," Twin Res, 2002, 5, 87-97.
Brindle et al., "Rapid and noninvasive diagnosis of the presence and severity of coronary heart disease using 1H-NMR-based metabonomics," Nat Med. 2002;8:1439-44.
Chace et al., "Rapid Diagnosis of Maple Syrup Urine Disease in Blood Spots from Newborns by Tandem Mass Spectrometry," Clin Chem, 1995, vol. 41 No. 1, pp. 62-68.
Chace et al.. Use of Tandem Mass Spectrometry for Multiananlyte Screening of Dried Blood Specimens from Newborns. Clinical Chemistry, 2003, vol. 49:11, 1797-1817.
DeLong et al., "Comparing the areas under two or more correlated receiver operating characteristic curves: a nonparametric approach," Biometrics, 1988, vol. 44, No. 3, pp. 837-845.
Ellis et al., Metabolic Fingerprinting as a Diagnostic Tool, Pharmacogenomics, 2007, vol. 8(9).
Ferdinandusse et al., "Identification of the peroxisomal beta-oxidation enzymes involved in the degradation of long-chain dicarboxylic acids," J Lipid Res. 2004;45:1104-11.
Ferrara et al., "Genetic networks of liver metabolism revealed by integration of metabolic and transcriptional profiling," PLoS Genet. 2008;4:e1000034.
Ferrara, C. T., "Metabolic Pathways of Type 2 Diabetes. Intersection of Genetics, Transcriptomics, and Metabolite Profiling," Dissertation (2008) Department of Pharmacology and Cancer Biology, Duke University (available on ProQuest in 2008).
Haqq et al., "The Study of the Effects of Diet on Metabolism and Nutrition (STEDMAN) weight loss project: Rationale and design," Contemp Clin Trials, 2005, vol. 26, pp. 616-625.
Hauser et al., "Design of the Genetics of Early Onset Cardiovascular Disease (GENECARD) study," Am Heart J, 2003, 145, pp. 602-613.
Johnson and Wichern D.W., 1988, Applied Multivariate Statistical Analysis. Prentice Hall, Englewood Cliffs, New Jersey.

Kaiser, "The Application of Electronic Computers to Factor Analysis," Educational and Psychological Measurement, 1960, vol. 20, pp. 141-151.
Keurentjes et al., "The genetics of plant metabolism," Nat Genet, 2006;38, pp. 842-849.
Kirschenlohr et al., "Proton NMR analysis of plasma is a weak predictor of coronary artery disease," Nat Med. 2006, 12, pp. 705-710.
Koves et al., "Mitochondrial overload and incomplete fatty acid oxidation contribute to skeletal muscle insulin resistance," Cell Metab, 2008, 7, 45-56.
Koves et al., "Peroxisome proliferator-activated receptor-gamma co-activator 1alpha-mediated metabolic remodeling of skeletal myocytes mimics exercise training and reverses lipid-induced mitochondrial inefficiency," J Biol Chem, 2005, 280, 33588-33598.
Lawlor et al., "(Mis)use of Factor Analysis in the Study of Insulin Resistance Syndrome," Am J Epidemiol, 2004, vol. 159, pp. 1013-1018.
Lum H et al. "Plasma Acylcarnitines Are Associated With Physical Performance in Elderly Men," J Gerontol A Biol Sci Med Sci. May 2011; 66A (5):548-553.
Millington et al., "Tandem mass spectrometry: a new method for acylcarnitine profiling with potential for neonatal screening for inborn errors of metabolism.," J Inherit Metab Dis, 1990, vol. 13, pp. 321-324.
Moselhy et al., "Serum free L-carnitine in association with myoglobin as a diagnostic marker of acute myocardial infarction," Clinical Biochemistry, Elsevier Inc, US, CA, vol. 42, No. 1-2, Sep. 30, 2008, pp. 78-82, XP025801716.
Muoio et al., "Mechanisms of disease: molecular and metabolic mechanisms of insulin resistance and beta-cell failure in type 2 diabetes," Nat Rev Mol Cell Biol, 2008, 9, 193-205.
Nakamura, T. et al., "Can Serum Carnitine Levels Distinguish Hypertrophic Cardiomyopathy From Hypertensive Hearts?" Hypertension, 2000, 36: 215-219.
Neubauer S. "The Failing Heart—An Engine Out of Fuel," N Engl J Med. 2007, 1140-1151.
Newgard et al., "A branched-chain amino acid-related metabolic signature that differentiates obese and lean humans and contributes to insulin resistance," Cell Metab, 2009, vol. 9, No. 4, pp. 311-326.
Nobukuni et al., "Amino acids mediate mTOR/raptor signaling through activation of class 3 phosphatidylinositol 3OH-kinase," Proc Natl Acad Sci U S A. 2005;102:14238-43.
Patterson et al., "Validation of a new procedure to determine plasma fatty acid concentration and isotopic enrichment," J Lipid Res, 1999, vol. 40, pp. 2118-2124.
Petersen et al., "Mitochondrial dysfunction in the elderly: possible role in insulin resistance," Science, 2003, 300, 1140-1142.
Rissanen, Familial occurrence of coronary heart disease: effect of age at diagnosis. Am J Cardiol, 1979, 44, 60-66.
Rosamond et al., "Heart Disease and Stroke Statistics—2007 Update: A Report From the American Heart Association Statistics Committee and Stroke Statistics Subcommittee," Circulation, 2007;115:e69-171.
Sabatine et al., "Metabolomic identification of novel biomarkers of myocardial ischemia," Circulation. 2005;112:3868-75.
Shah A et al. "Metabolic profiles predict adverse events after coronary artery bypass grafting," JTCS. 2012, 872-878.
Shah et al., "Baseline metabolomic profiles predict cardiovascular events in patients at risk for coronary artery disease." American Heart Journal, 163, May 5, 2012, 844-850.
Shah et al., "High heritabilities of serum metabolites and differential metabolomic profiles in families burdened with early onset coronary artery disease," Circulation, vol. 114, No. 18, Suppl. S, Oct. 2006, p. 677, XP002717079.
Shah et al., "High heritability of metabolomic profiles in families burdened with premature cardiovascular disease," Mol Syst Biol, 2009, 5, p. 258.
Shah et al., "Serum lipids in the GENECARD study of coronary artery disease identify quantitative trait loci and phenotypic subsets on chromosomes 3q and 5q," Ann Hum Genet, 2006, 70, 738-748.

(56) References Cited

OTHER PUBLICATIONS

Shah SH et al. "Association of a Peripheral Blood Metabolic Profile With Coronary Artery Disease and Risk of Subsequent Cardiovascular Events," Circ Cardiovasc Genet. 2010, 207-214.
Sharma Kand Kass DA. "Heart Failure With Preserved Ejection Fraction Mechanisms, Clinical Features, and Therapies," Circulation Research. 2014, 79-96.
Shea et al., "Family history as an independent risk factor for coronary artery disease," J Am Coll Cardiol, 1984, 4, 793-801.
Smith et al., "Determinants of early versus late cardiac death in patients undergoing coronary artery bypass graft surgery," Circulation. 84[5 Suppl], III245-253. 1991.
Um et al., "Nutrient overload, insulin resistance, and ribosomal protein S6 kinase 1, S6K1," Cell Metab. 2006;3:393-402.
World Health Organization. The World Health Report 2002—Reducing Risks, Promoting Healthy Life. 2002.
Wu et al., "ENU mutagenesis identifies mice with mitochondrial branched-chain aminotransferase deficiency resembling human maple syrup urine disease," J Clin Invest, 2004, vol. 113, pp. 434-440.
Search Report from International Patent Application PCT/US2010/026845, dated Apr. 27, 2010.
International Search Report and Written Opinion for Application No. PCT/US2016/022388 dated May 26, 2016 (13 pages).
United States Patent Office Action for U.S. Appl. No. 13/255,568 dated Jan. 21, 2015 (15 pages).
United States Patent Office Final Action for U.S. Appl. No. 13/255,568 dated Sep. 10, 2015 (17 pages).
United States Patent Office Action for U.S. Appl. No. 15/066,837 dated Oct. 7, 2016 (13 pages).
United States Patent Office Action for U.S. Appl. No. 15/066,837 dated Jul. 14, 2017 (11 pages).
United States Patent Office Action for U.S. Appl. No. 15/066,837 dated Nov. 16, 2007 (11 pages).
United States Patent Office for U.S. Appl. No. 15/066,837 dated Sep. 12, 2018 (8 pages).
United States Patent Office Notice of Allowance for U.S. Appl. No. 15/066,837 dated Jan. 24, 2019 (8 pages).

* cited by examiner

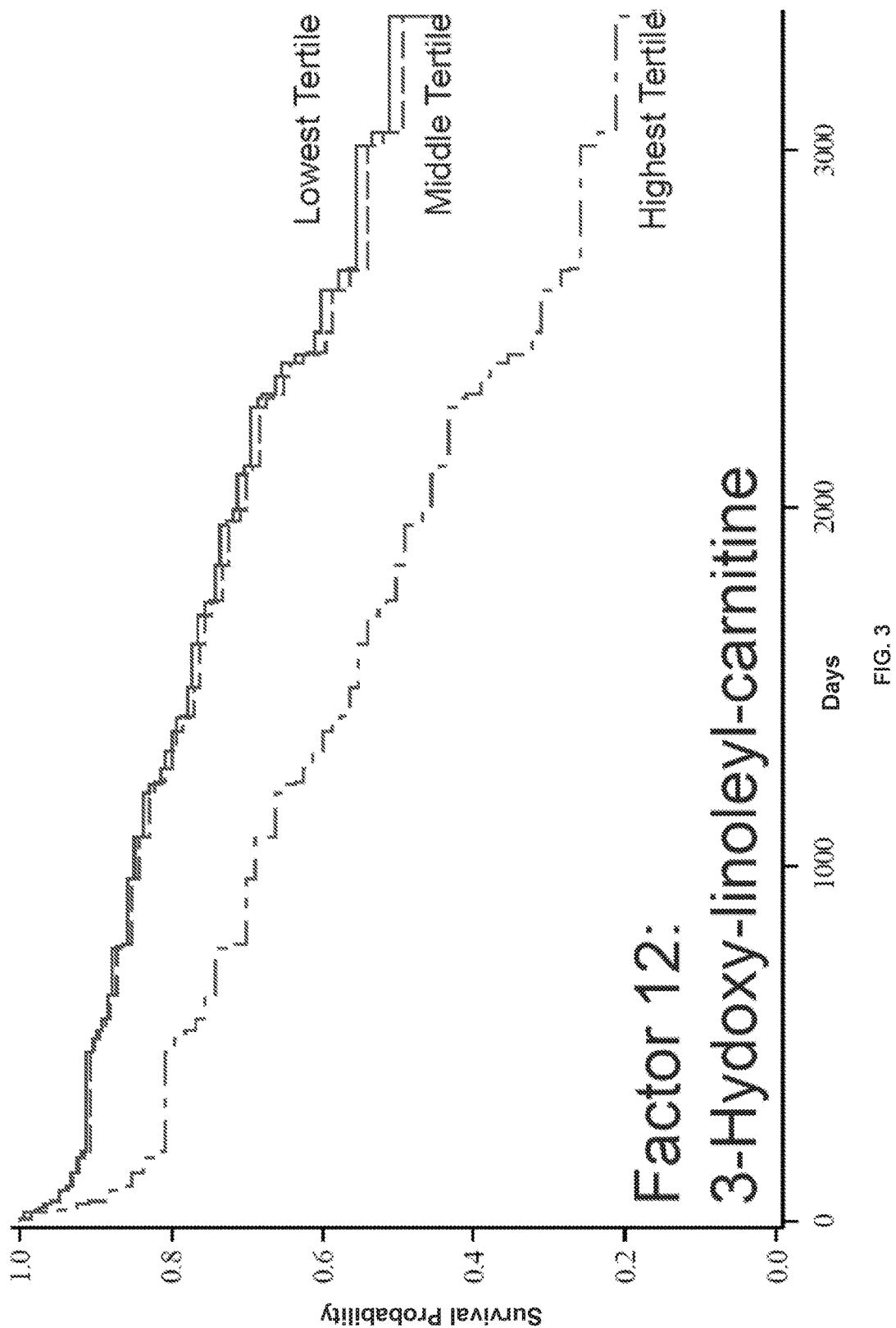

COMPOSITIONS AND METHODS FOR METABOLIC PROFILING IN SUBJECTS WITH HEART FAILURE WITH PRESERVED EJECTION FRACTION

CROSS-REFERENCE TO RELATED APPLICATIONS

This application is a U.S. national stage filing under 35 U.S.C. 371 of International Application No. PCT/US2016/022388, filed Mar. 14, 2016, which claims priority to U.S. Provisional Patent Application No. 62/132,848, filed Mar. 13, 2015, each of which is incorporated herein by reference in its entirety.

STATEMENT REGARDING FEDERALLY SPONSORED RESEARCH

This invention was made with government support under Federal Grant Nos. HL095987 and HL101621-01 awarded by the National Institutes of Health. The government has certain rights in the invention.

FIELD

This disclosure relates to compositions and methods including biomarkers for heart failure with preserved ejection fraction.

INTRODUCTION

Metabolic and bioenergetic abnormalities have been implicated in the pathogenesis of heart failure with reduced ejection fraction (HFrEF). Some have proposed that abnormal metabolism also contributes to the pathogenesis of heart failure with preserved ejection fraction (HFpEF). However, biomarkers that discriminate HFpEF and risk prediction models in heart failure with preserved ejection fraction (HFpEF) remain incomplete. Novel molecular biomarkers are needed to improve diagnostics and risk stratification in this clinically heterogeneous patient population.

SUMMARY

In an aspect, the disclosure relates to a method for assessing risk of death or a major adverse cardiac event (MACE) in a subject diagnosed with heart failure with preserved ejection fraction (HFpEF). The method may include (a) determining in a sample from the subject the level of each metabolite in at least one factor, wherein the factor is selected from the group consisting of factor 1, factor 3, factor 4, factor 5, factor 10, factor 12, and factor 14; and (b) comparing the level of each metabolite in the sample to a standard, wherein the level of the metabolite in the subject relative to a standard is indicative of the risk of death or MACE in the subject. In some embodiments, factor 1 consists of medium-chain acylcarnitines. In some embodiments, factor 3 consists of short-chain dicarboxylacylcarnitines. In some embodiments, factor 4 consists of long-chain acylcarnitines. In some embodiments, factor 5 consists of ketone related metabolites. In some embodiments, factor 10 consists of glycine, ornithine, and tiglyl-carnitine. In some embodiments, factor 12 consists of 3-hydroxy-linoleyl-carnitine. In some embodiments, factor 14 consists of docosanoyl-carnitine. In some embodiments, the method further includes determining that the subject has a risk of death or MACE when the level of each metabolite in the subject is different from the standard. In some embodiments, the method further includes determining the level of each metabolite in factor 1, wherein an increased level of the metabolite in the subject is indicative of the risk of death or MACE in the subject. In some embodiments, the method further includes determining the level of each metabolite in factor 3, wherein an increased level of the metabolite in the subject is indicative of the risk of death or MACE in the subject. In some embodiments, the method further includes determining the level of each metabolite in factor 4, wherein an increased level of the metabolite in the subject is indicative of the risk of death or MACE in the subject. In some embodiments, the method further includes determining the level of each metabolite in factor 5, wherein an increased level of the metabolite in the subject is indicative of the risk of death or MACE in the subject. In some embodiments, the method further includes determining the level of each metabolite in factor 12, wherein an increased level of the metabolite in the subject is indicative of the risk of death or MACE in the subject. In some embodiments, the method further includes comprising determining the level of each metabolite in factor 10, wherein a decreased level of the metabolite in the subject is indicative of the risk of death or MACE in the subject. In some embodiments, the method further includes comprising determining the level of each metabolite in factor 14, wherein a decreased level of the metabolite in the subject is indicative of the risk of death or MACE in the subject.

In a further aspect, the disclosure relates to a method for assessing risk of death or MACE in a subject diagnosed with HFpEF. The method may include (a) determining in a sample from the subject the level of each metabolite in at least one factor selected from the group consisting of factor 1, factor 3, factor 4, factor 5, factor 10, factor 12, and factor 14, wherein factor 1 consists of medium-chain acylcarnitines, wherein factor 3 consists of short-chain dicarboxylacylcarnitines, wherein factor 4 consists of long-chain acylcarnitines, wherein factor 5 consists of ketone related metabolites, wherein factor 10 consists of glycine, ornithine, and tiglyl-carnitine, wherein factor 12 consists of 3-hydroxy-linoleyl-carnitine, and wherein factor 14 consists of docosanoyl-carnitine; (b) calculating a weighted level of each metabolite by multiplying the determined level by a scoring coefficient specific for each metabolite; (c) adding the weighted level of each metabolite in the factor together to yield a factor score; (d) comparing the factor score of the sample to a non-HFpEF standard; and (e) determining that the subject has an increased risk of death or MACE when the factor score in the subject is different from the standard. In some embodiments, the method further includes determining the level of each metabolite in factor 1, wherein an increased level of the factor score for the subject is indicative of the risk of death or MACE in the subject. In some embodiments, the method further includes determining the level of each metabolite in factor 3, wherein an increased level of the factor score for the subject is indicative of the risk of death or MACE in the subject. In some embodiments, the method further includes determining the level of each metabolite in factor 4, wherein an increased level of the factor score for the subject is indicative of the risk of death or MACE in the subject. In some embodiments, the method further includes determining the level of each metabolite in factor 5, wherein an increased level of the factor score for the subject is indicative of the risk of death or MACE in the subject. In some embodiments, the method further includes determining the level of each metabolite in factor 12, wherein an increased level of the factor score for the subject is indicative of the risk of death or MACE in the subject. In some embodiments, the method further includes determining the level of each metabolite in factor 10, wherein a decreased level of the factor score for the subject is indicative of the risk of death or MACE in the subject. In some embodiments, the method further includes determining the level of each metabolite in factor 14, wherein a decreased level of the factor score for the subject is indicative of the risk of death or MACE in the subject.

In some embodiments, factor 1 consists of medium-chain acylcarnitines selected from C8, C10, C12, C14:1, C14, C16:2, C16:1, C14:2, C12:1, and C10:1 acylcarnitines. In some embodiments, factor 3 consists of short-chain dicarboxylacylcarnitines selected from C5-DC, C6:1-DC/C8:1-OH, C8:1-DC, C6-DC, Ci4-DC/C4-DC, C10-OH/C8-DC, and C12-OH/C10-DC acylcarnitines and the amino acid citrulline. In some embodiments, factor 4 consists of long-chain acylcarnitine related metabolites selected from C18:1, C18:2, C18, C16, C20:4, and C16:1-OH/C14:1-DC acylcarnitines. In some embodiments, factor 5 consists of ketone related metabolites selected from ketones, ß-hydroxybutyrate, ß-hydroxybutyryl-carnitine, acetylcarnitine, and alanine.

In some embodiments, the level of each metabolite in more than one factor is determined in step (a). In some embodiments, the level of each metabolite in two factors is determined in step (a). In some embodiments, the level of each metabolite in three factors is determined in step (a). In some embodiments, the level of each metabolite in four factors is determined in step (a). In some embodiments, the level of each metabolite in five factors is determined in step (a). In some embodiments, the level of each metabolite in six factors is determined in step (a).

Another aspect of the disclosure provides a method of developing a treatment plan for a subject comprising steps (a) and (b) of claim 1, and further comprising (c) determining that the subject has a risk of death or MACE when the level of each metabolite in the subject is different from the standard; and (d) developing a treatment plan when the subject is determined in step (c) to have a risk of death or MACE. In some embodiments, the treatment plan comprises at least one therapy selected from the group consisting of lifestyle modification, angiotensin converting enzyme inhibitors, angiotensin receptor blocker, beta blocker, aldosterone antagonist, hydralazine, nitrate, pacemaker, implantable cardiac defibrillator, and heart transplant, or a combination thereof.

Another aspect of the disclosure provides a method for diagnosing heart failure with preserved ejection fraction (HFpEF) in a subject. The method may include (a) determining in a sample from the subject the level of each metabolite in factor 4; and (b) comparing the level of each metabolite in the sample to a standard, wherein the level of the metabolite in the subject relative to a standard is indicative of the subject having HFpEF, wherein factor 4 consists of long chain acylcarnitines. In some embodiments, factor 4 consists of long-chain acylcarnitine related metabolites selected from C18:1, C18:2, C18, C16, C20:4, and C16:1-OH/C14:1-DC acylcarnitines. In some embodiments, the method further includes identifying the subject as having HFpEF when the level of each metabolite in the subject is greater than the standard.

In some embodiments, the sample is blood. In some embodiments, the level of the metabolite is detected using mass spectrometry. In some embodiments, the level of the metabolite is detected using a colorimetric or fluorometric assay.

The disclosure provides for other aspects and embodiments that will be apparent in light of the following detailed description and accompanying figures.

BRIEF DESCRIPTION OF THE DRAWINGS

FIG. 3 is the adjusted survival curve showing the relationship between tertiles of metabolite factor 12 (3-hydroxy-linoleyl-carnitine) and mortality.

DETAILED DESCRIPTION

Figure 1:
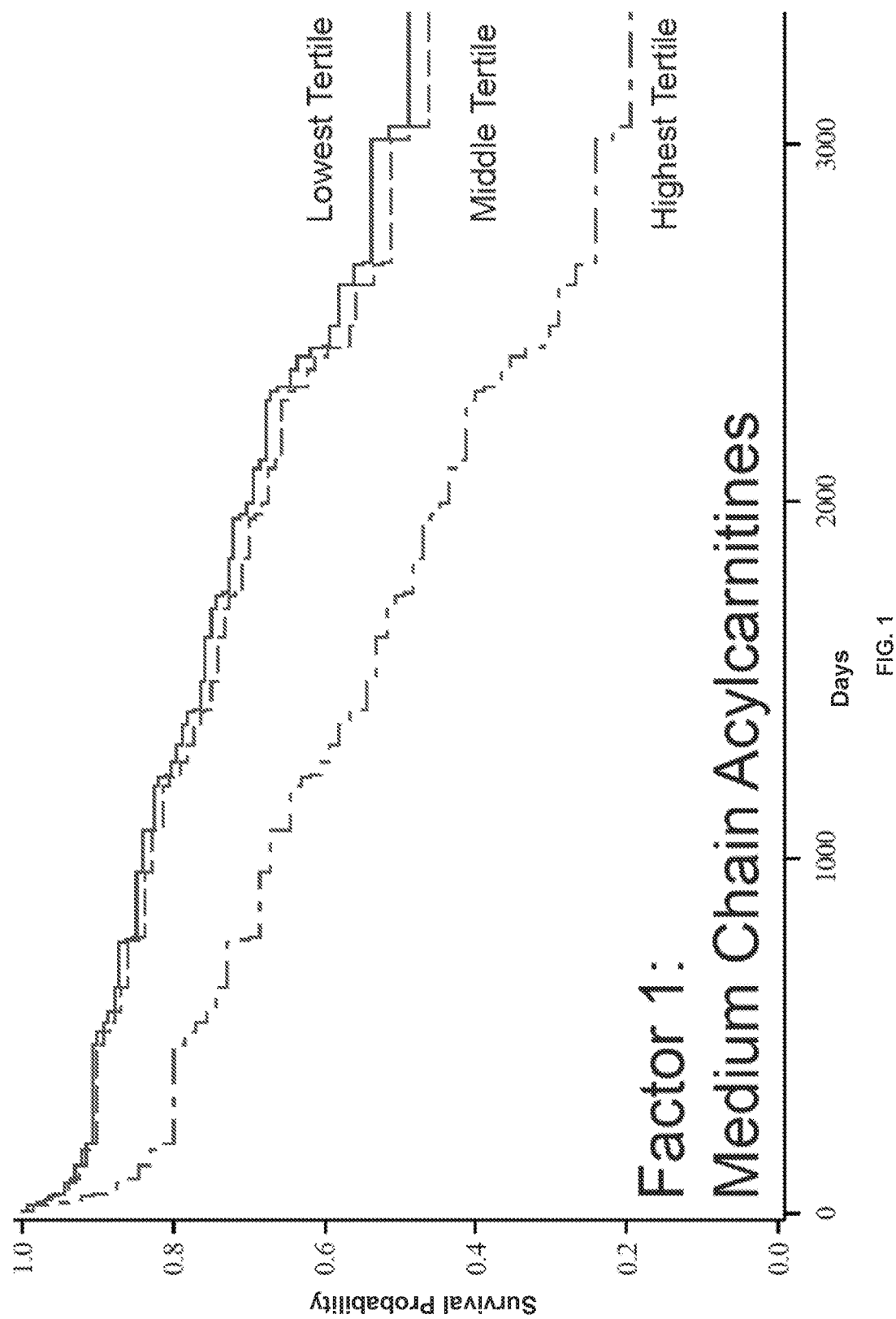
FIG. 1 is the adjusted survival curve showing the relationship between tertiles of metabolite factor 1 (medium chain acylcarnitines) and mortality.
Figure 2:
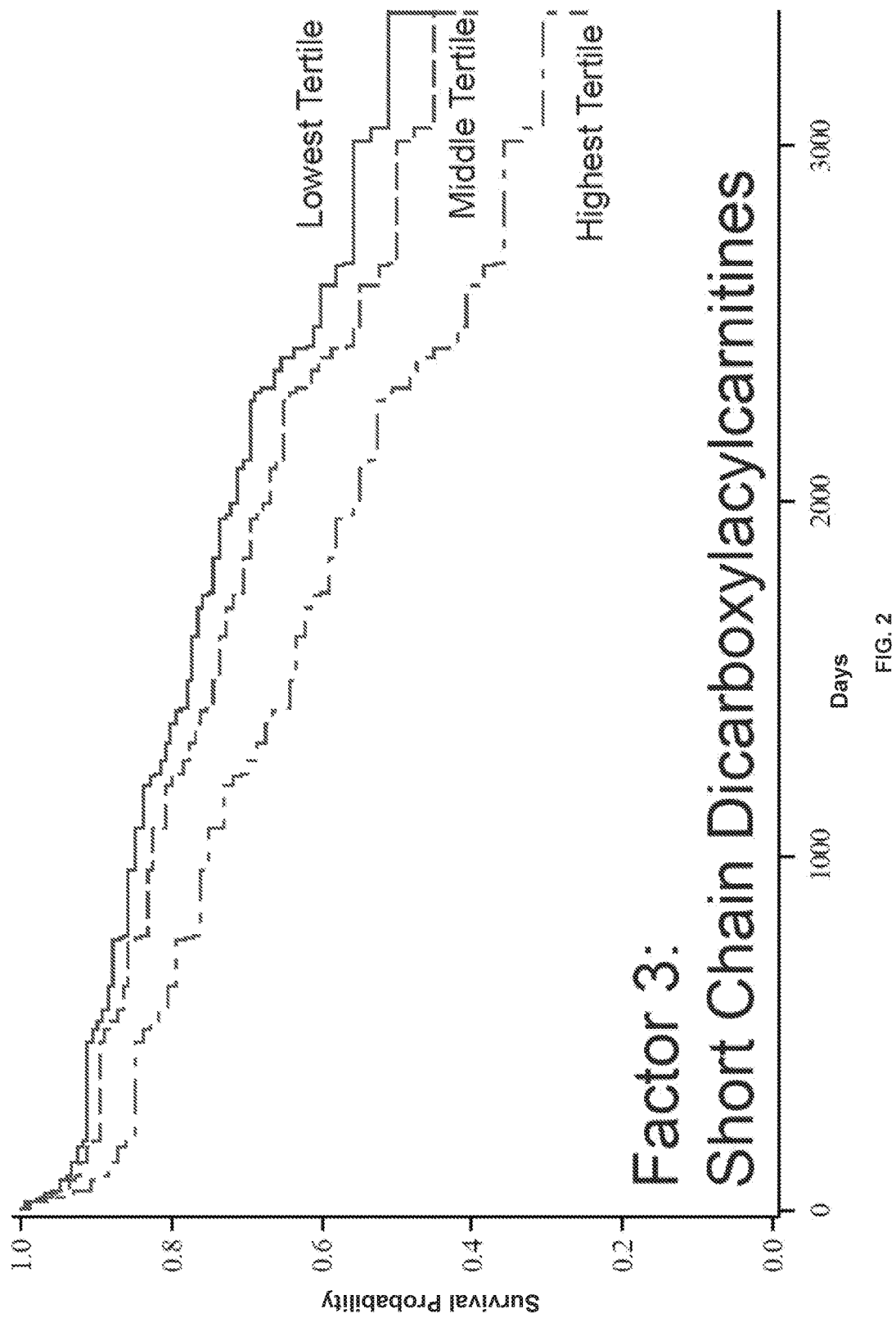
FIG. 2 is the adjusted survival curve showing the relationship between tertiles of metabolite factor 3 (short chain dicarboxylacylcarnitines) and mortality.

The present disclosure relates to biomarkers for major adverse cardiac events and/or death in subjects with heart failure with preserved ejection fraction, as well as to biomarkers for discrimination of patients with heart failure with preserved ejection fraction. Targeted metabolomic profiling provides a quantification of a broad array of metabolic intermediates of fatty acid, amino acid, and carbohydrate metabolism. Compositions and methods may be used for targeting metabolomics profiling to identify metabolites in peripheral blood that are independently associated with HFpEF itself and with survival or major adverse cardiac events in patients with HFpEF. Provided herein are methods for detecting and/or quantifying the levels of biomarkers including, for example, long-chain acylcarnitines, medium-chain acylcarnitines, short-chain dicarboxylacylcarnitines, ketone related metabolites, glycine, ornithine, tiglyl-carnitine, 3-hydroxy-linoleyl-carnitine, and docosanoyl-carnitine. The methods disclosed herein may be used for identifying HFpEF patients. The methods disclosed herein may also be used for identifying, diagnosing, prognosing, classifying risk, and/or monitoring a major adverse cardiac events and/or death in subjects with heart failure with preserved ejection fraction.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Acylcarnitines" are fatty acyl esters of L-carnitine. "Carnitine" is an amino acid derivative and nutrient involved in lipid metabolism in mammals and other eukaryotes. Carnitine is in the chemical compound classes of β-hydroxyacids and quaternary ammonium compounds, and because of the hydroxyl-substituent, it exists in two stereoisomers: the biologically active enantiomer L-carnitine, and the essentially biologically inactive D-carnitine. Carnitine transports long-chain acyl groups from fatty acids from the intermembraneous space in the mitochondria into the mitochondrial matrix during the catabolism of lipids so they can be broken down through β-oxidation to acetyl CoA to obtain usable energy via the citric acid cycle.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The "area under curve" or "AUC" refers to area under a ROC curve. AUC under a ROC curve is a measure of accuracy. An area of 1 represents a perfect test, whereas an area of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, TEXAS RED (Molecular Probes, Inc.), and CASCADE blue acetylazide (Molecular Probes, Inc.). An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 2006, 16, 1324-1328; Adamczyk et al., Bioorg. Med. Chem. Lett. 2004, 4, 2313-2317; Adamczyk et al., Biorg. Med. Chem. Lett. 2004, 14, 3917-3921; and Adamczyk et al., Org. Lett. 2003, 5, 3779-3782).

In one aspect, the acridinium compound is an acridinium-9-carboxamide. Methods for preparing acridinium 9-carboxamides are described in Mattingly, J. Biolumin. Chemilumin. 1991, 6, 107-114; Adamczyk et al., J. Org. Chem. 1998, 63, 5636-5639; Adamczyk et al., Tetrahedron 1999, 55, 10899-10914; Adamczyk et al., Org. Lett. 1999, 1, 779-781; Adamczyk et al., Bioconjugate Chem. 2000, 11, 714-724; Mattingly et al., In Luminescence Biotechnology: Instruments and Applications; Dyke, K. V. Ed.; CRC Press: Boca Raton, pp. 77-105 (2002); Adamczyk et al., Org. Lett. 2003, 5, 3779-3782; and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 1965, 4, 1111-21; Razavi et al., Luminescence 2000, 15, 245-249; Razavi et al., Luminescence 2000, 15, 239-244; and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier 2003). The amount of protein removed or separated from the test sample can be about 40%, about 45%, about 50%, about 55%, about 60%, about 65%, about 70%, about 75%, about 80%, about 85%, about 90%, or about 95%. Acridinium-9-carboxylate aryl esters can be dissolved in any suitable solvent, such as degassed anhydrous N,N-dimethylformamide (DMF) or aqueous sodium cholate.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of amino acids and can be natural, synthetic, or a modification or combination of natural and synthetic. Peptides and polypeptides include proteins such as binding proteins. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units.

"Predetermined cutoff" and "predetermined level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). Cutoff values may vary depending on the nature of the immunoassay (e.g., antibodies employed, reaction conditions, sample purity, etc.). It is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample" or "biological sample" or "test sample" as used herein can mean any sample in which the presence and/or level of a biomarker is to be detected or determined. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, lung tissue, peripheral blood mononuclear cells (PBMC), total white blood cells, monocytes, lymph node cells, spleen cells, tonsil cells, skin, or combinations thereof. In some embodiments, the sample comprises a biological fluid. In some embodiments, the sample comprises blood, whole blood, plasma, serum, PBMCs, monocytes, or a combination thereof. In some embodiments, the sample comprises blood, PBMCs, monocytes, or a combination thereof. In some embodiments, the sample comprises monocytes. Monocytes may be isolated from whole blood. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

The term "sensitivity" as used herein refers to the number of true positives divided by the number of true positives plus the number of false negatives, where sensitivity ("sens") may be within the range of 0<sens<1. Ideally, method embodiments herein have the number of false negatives equaling zero or close to equaling zero, so that no subject is wrongly identified as not having hypertension or inflammation when they indeed have hypertension or inflammation. Conversely, an assessment often is made of the ability of a prediction algorithm to classify negatives correctly, a complementary measurement to sensitivity.

The term "specificity" as used herein refers to the number of true negatives divided by the number of true negatives plus the number of false positives, where specificity ("spec") may be within the range of 0<spec<1. Ideally, the methods described herein have the number of false positives equaling zero or close to equaling zero, so that no subject is wrongly identified as having hypertension or inflammation when they do not in fact have hypertension or inflammation. Hence, a method that has both sensitivity and specificity equaling one, or 100%, is preferred.

"Subject" or "patient" as used herein refers to any subject, particularly a mammalian subject, who wants to or is in need of detecting a biomarker. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject is human.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

U.S. patent application Ser. No. 13/255,568, which was filed Sep. 9, 2011, and published as U.S. Patent Application Publication No. US 2011-0318726 on Dec. 29, 2011, is incorporated herein by reference. If there is any conflict between the present disclosure and US 2011-0318726, then the present disclosure controls.

2. Disease

The present disclosure relates to detecting, analyzing, or quantifying the levels of one or more biomarkers for assessing the risk of, diagnosing, and prognosing a disease in a subject. As used herein, "disease" may be referred to as a "condition" and vice versa. The biomarkers may be used as targets for treating or preventing a disease. The disease may include heart failure. The disease may include heart failure with preserved ejection fraction. The condition may include a major adverse cardiac event or death. In some embodiments, the subject has heart failure with preserved ejection fraction.

a. Heart Failure

Heart failure (HF) is a physiological state in a subject when heart is unable to pump sufficiently to maintain blood flow to meet the body's needs. In heart failure, cardiac output is insufficient to meet the needs of the body and lungs. Heart failure may also be referred to as congestive heart failure, as one of the common symptoms is congestion, which is the build-up of too much fluid in tissues and veins. Signs and symptoms of heart failure may include shortness of breath, excessive tiredness, and leg swelling. Congestion may include, for example, water retention, edema including peripheral edema and pulmonary edema, and ascites. The shortness of breath may worsen with exercise, while lying down, and may wake the subject at night. A limited ability to exercise is also a common feature. Heart failure is caused by any condition which reduces the efficiency of the heart muscle, through damage or overloading. Heart failure may be caused by coronary artery disease including a previous myocardial infarction (heart attack), high blood pressure, atrial fibrillation, valvular heart disease, excess alcohol use, infection, and cardiomyopathy of an unknown cause.

Heart failure is divided into two different types: heart failure due to reduced ejection fraction (HFrEF; also known as heart failure due to left ventricular systolic dysfunction or systolic heart failure) and heart failure with preserved ejection fraction (HFpEF; also known as diastolic heart failure or heart failure with normal ejection fraction). HFrEF occurs when the ejection fraction is less than 40%. Ejection fraction is the proportion of blood pumped out of the heart during a single contraction. Ejection fraction is given as a percentage, with the normal range being between 50% and 75%. In HFpEF, the heart muscle contracts well but the ventricle does not fill with blood well in the relaxation phase.

Treatment for heart failure may include treatment lifestyle modifications such as smoking cessation, physical exercise, and dietary changes. Treatment may include more aggressive treatment of related risk factors. Treatment may include more aggressive treatment of downstream consequences of HFpEF that are related to MACEs. Treatment for heart failure may also include therapies such as, for example, angiotensin converting enzyme inhibitors, angiotensin receptor blockers, beta blockers, aldosterone antagonists, hydralazine, nitrates, or a combination thereof. Treatments may also include pacemakers, an implantable cardiac defibrillator, or a heart transplant.

b. MACE

A major adverse cardiac event (MACE) is a composite of clinical events and includes at least one of unsuspected heart attacks (also known as acute myocardial infarction), cardiac death, atrial fibrillation, non-fatal myocardial infarction, unstable angina, and target lesion revascularization, and combinations thereof. Myocardial infarction occurs when blood flow stops to a part of the heart, causing damage to the heart muscle. Sudden cardiac death is a sudden, unexpected death caused by loss of heart function. Unstable angina is angina pectoris caused by disruption of an atherosclerotic plaque with partial thrombosis and possibly embolization or vasospasm. Angina pectoris is the sensation of chest pain, pressure, or squeezing, which may be due to ischemia of the heart muscle from obstruction or spasm of the coronary arteries.

3. Biomarkers

The methods detailed herein include detecting and/or measuring the level of one or more biomarkers in a sample. A change or difference in the level of the biomarker in the sample obtained from the subject relative to a standard indicates the subject is suffering from or is at risk of suffering from the disease. In some embodiments, the change in the level of the biomarker may be an increase relative to the standard. Such an increase in the level of the biomarker may indicate that the subject is suffering from or is at risk of suffering from the disease. In some embodiments, the change in the level of the biomarker may be a decrease relative to the standard. Such a decrease in the level of the biomarker may indicate that the subject is suffering from or is at risk of suffering from the disease. In some embodiments, the biomarker includes one or more metabolites listed in TABLE 1. In some embodiments, the biomarker includes the metabolites of one or more of the factors listed in TABLE 4. In some embodiments, the biomarker includes one or more of factor 1, factor 3, factor 4, factor 5, factor 10, factor 12, factor 14, or any combination thereof. In some embodiments, the biomarker includes the metabolites of one or more of factor 1, factor 3, factor 4, factor 5, factor 10, factor 12, factor 14, or any combination thereof.

TABLE 1

List of measured metabolites.

| Abbreviate Name* | Full Name |
|---|---|
| C2 | Acetyl carnitine |
| C3 | Propionyl carnitine |
| C4/Ci4 | Butyryl carnitine or isobutyryl carnitine |
| C5:1 | Tiglyl carnitine or 3-methyl crotonyl carnitine |
| C5 | Isovaleryl, 3-methylbutyryl carnitine, 2-Methylbutyryl, valeryl or pivaloyl carnitine |
| C4-OH | D-3-Hydroxy-butyryl carnitine, L-3-hydroxybutyryl carnitine |
| C6 | Hexanoyl carnitine |
| C5-OH/C3-DC | 3-Hydroxy-isovaleryl carnitine or malonyl carnitine |
| Ci4-DC/C4-DC | Methylmalonyl carnitine or succinyl carnitine |
| C8:1 | Octenoyl carnitine† |
| C8 | Octanoyl carnitine |
| C5-DC | Glutaryl carnitine, ethylmalonyl carnitine |
| C8:1-OH/C6:1-DC | 3-Hydroxy-octenoyl carnitine or hexenedioyl carnitine |
| C8-OH/C6-DC | 3-hydroxy octanoyl carnitine or adipoyl carnitine, 3-methylglutaryl carnitine |
| C10:3 | Decatrienoyl carnitine† |
| C10:2 | Decadienoyl carnitine† |
| C10:1 | Decenoyl carnitine† |
| C10 | Decanoyl carnitine |
| C7-DC | Pimeloyl carnitine, heptanedioyl carnitine |
| C10:1-OH/C8:1-DC | 3-Hydroxy-decenoyl carnitine or octadecenedioyl carnitine |
| C10-OH/C8-DC | 3-Hydroxy-decanoyl carnitine or suberoyl carnitine |
| C12:1 | Dodecenoyl carnitine† |
| C12 | Lauroyl carnitine |
| C12-OH/C10-DC | 3-Hydroxy-dodecanoyl carnitine or sebacoyl carnitine |
| C14:2 | Tetradecadienoyl carnitine† |
| C14:1 | Tetradecenoyl carnitine† |
| C14 | Myristoyl carnitine |
| C14:1-OH/C12:1-DC | 3-Hydroxy-tetradecenoyl carnitine or dodecenedioyl carnitine |
| C14-OH/C12-DC | 3-Hydroxy-tetradecanoyl carnitine or dodecanedioyl carnitine |
| C16:2 | Hexadecadienoyl carnitine† |
| C16:1 | Palmitoleoyl carnitine† |
| C16 | Palmitoyl carnitine |
| C16:1-OH/C14:1-DC | 3-Hydroxy-palmitoleoyl carnitine or cis-5-tetradecenedioyl carnitine |
| C16-OH/C14-DC | 3-Hydroxy-hexadecanoyl carnitine or tetradecanedioyl carnitine |
| C18:2 | Linoleyl carnitine |
| C18:1 | Oleyl carnitine |
| C18 | Stearoyl carnitine |
| C18:2-OH/C16:2-DC | 3-Hydroxy-linoleyl carnitine or hexadecadienedioyl carnitine |
| C18:1-OH/C16:1-DC | 3-Hydroxy-octadecenoyl carnitine or hexadecanedioyl carnitine |
| C18-OH/C16-DC | 3-Hydroxy-octadecanoyl carnitine or hexadecanedioyl carnitine, thapsoyl carnitine |
| C20:4 | Arachidonoyl carnitine |
| C20 | Arachidoyl carnitine, eicosanoyl carnitine |
| C18:1-DC | Octadecenedioyl carnitine |
| C20-OH/C18-DC/ C22:6 | 3-Hydroxy-eicosanoyl carnitine or octadecanedioyl carnitine or docosahexaenoyl carnitine |
| C22 | Docosanoyl carnitine, Behenoyl carnitine |
| GLY | Glycine |
| ALA | Alanine |
| SER | Serine |
| PRO | Proline |
| VAL | Valine |
| LEU/ILE | Leucine/Isoleucine |
| MET | Methionine |
| HIS | Histidine |
| PHE | Phenylalanine |
| TYR | Tyrosine |
| ASX | Aspartic acid/asparagine |
| GLX | Glutamine/glutamate |
| ORN | Ornithine |
| CIT | Citrulline |

TABLE 1-continued

List of measured metabolites.

| Abbreviate Name* | Full Name |
|---|---|
| ARG | Arginine |
| FFA | Total free fatty acids |
| HBUT | β-Hydroxybutyrate |
| KET | Ketones |

*Some metabolite isomers and isobars were not differentiated by flow injection tandem mass spectrometry; potential isomers or isobars are listed where applicable.
†Positions of double bond(s) uncertain.
Abbreviations:
C indicates acylcarnitine carbon chain length;
OH, hydroxyl;
DC, dicarboxyl.

a. Factor 1

Factor 1 consists of medium-chain acylcarnitines. The metabolites of factor 1 consist of medium-chain acylcarnitines selected from C8, C10, C12, C14:1, C14, C16:2, C16:1, C14:2, C12:1, and C10:1 acylcarnitines. In some embodiments, the level of at least one metabolite in factor 1 is determined. In some embodiments, the level of each metabolite in factor 1 is determined. In some embodiments, the level of at least one of C8, C10, C12, C14:1, C14, C16:2, C16:1, C14:2, C12:1, and C10:1 acylcarnitine is determined. In some embodiments, the level of each of C8, C10, C12, C14:1, C14, C16:2, C16:1, C14:2, C12:1, and C10:1 acylcarnitine is determined. An increase in the levels of factor 1 relative to the standard may indicate that the subject is suffering from or is at risk of suffering from the disease.

b. Factor 3

Factor 3 consists of short-chain dicarboxylacylcarnitines. The metabolites of factor 3 consist of short-chain dicarboxylacylcarnitines selected from C5-DC, C6:1-DC/C8:1-OH, C8:1-DC, C6-DC, Ci4-DC/C4-DC, C10-OH/C8-DC, and C12-OH/C10-DC acylcarnitine and the amino acid citrulline. In some embodiments, the level of at least one metabolite in factor 3 is determined. In some embodiments, the level of each metabolite in factor 3 is determined. In some embodiments, the level of at least one of C5-DC, C6:1-DC/C8:1-OH, C8:1-DC, C6-DC, Ci4-DC/C4-DC, C10-OH/C8-DC, and C12-OH/C10-DC acylcarnitine and the amino acid citrulline is determined. In some embodiments, the level of each of C5-DC, C6:1-DC/C8:1-OH, C8:1-DC, C6-DC, Ci4-DC/C4-DC, C10-OH/C8-DC, and C12-OH/C10-DC acylcarnitine and the amino acid citrulline is determined. An increase in the levels of factor 3 relative to the standard may indicate that the subject is suffering from or is at risk of suffering from the disease.

c. Factor 4

Factor 4 consists of long chain acylcarnitine metabolites. The metabolites of factor 4 consist of long chain acylcarnitines selected from C18:1, C18:2, C18, C16, C20:4, and C16:1-OH/C14:1-DC. In some embodiments, the level of at least one metabolite in factor 4 is determined. In some embodiments, the level of each metabolite in factor 4 is determined. In some embodiments, the level of at least one of C18:1, C18:2, C18, C16, C20:4, and C16:1-OH/C14:1-DC is determined. In some embodiments, the level of each of C18:1, C18:2, C18, C16, C20:4, and C16:1-OH/C14:1-DC is determined. An increase in the levels of factor 4 relative to the standard may indicate that the subject is suffering from or is at risk of suffering from the disease.

d. Factor 5

Factor 5 consists of ketone related metabolites. The metabolites of factor 5 consist of ketone related metabolites selected from ketones, beta-hydroxybutyrate, beta-hydroxybutyryl-carnitine, acetylcarnitine, and alanine. In some embodiments, the level of at least one metabolite in factor 5 is determined. In some embodiments, the level of each metabolite in factor 5 is determined. In some embodiments, the level of at least one of a ketone, beta-hydroxybutyrate, beta-hydroxybutyryl-carnitine, acetylcarnitine, and alanine is determined. In some embodiments, the level of each of a ketone, beta-hydroxybutyrate, beta-hydroxybutyryl-carnitine, acetylcarnitine, and alanine is determined. An increase in the levels of factor 5 relative to the standard may indicate that the subject is suffering from or is at risk of suffering from the disease.

e. Factor 10

Factor 10 consists of the metabolites glycine, ornithine, and tiglyl-carnitine. In some embodiments, the level of at least one metabolite in factor 10 is determined. In some embodiments, the level of each metabolite in factor 10 is determined. In some embodiments, the level of at least one of glycine, ornithine, and tiglyl-carnitine is determined. In some embodiments, the level of each of glycine, ornithine, and tiglyl-carnitine is determined. A decrease in the levels of factor 10 relative to the standard may indicate that the subject is suffering from or is at risk of suffering from the disease.

f. Factor 12

Factor 12 consists of the metabolite 3-hydroxy-linoleyl-carnitine. In some embodiments, the level of 3-hydroxy-linoleyl-carnitine is determined. An increase in the levels of factor 12 relative to the standard may indicate that the subject is suffering from or is at risk of suffering from the disease.

g. Factor 14

Factor 14 consists of docosanoyl-carnitine. In some embodiments, the level of docosanoyl-carnitine is determined. A decrease in the levels of factor 14 relative to the standard may indicate that the subject is suffering from or is at risk of suffering from the disease.

h. Scoring Coefficient

In some embodiments, the detected amount or level of each metabolite in a factor may be multiplied by a scoring coefficient specific for each metabolite to result in a weighted level of each metabolite. The weighted level of each metabolite in the same factor may be added together to yield a factor score. In some embodiments, the factor score is compared to a standard. A change in the factor score relative to the standard may indicate that the subject is suffering from or is at risk of suffering from the disease. In some embodiments, the factor score may be greater than the standard. In some embodiments, the factor score may be less than the standard.

Scoring coefficients for each metabolite in each factor are shown in TABLE 2A and TABLE 2B.

TABLE 2A

Scoring coefficients for metabolite factors 1-7.

| Metabolite | Factor 1 | Factor 2 | Factor 3 | Factor 4 | Factor 5 | Factor 6 | Factor 7 |
|---|---|---|---|---|---|---|---|
| Gly | 0.0062 | −0.0008 | −0.0215 | −0.0127 | 0.0143 | 0.0223 | −0.1004 |
| Ala | 0.0203 | 0.0205 | −0.0465 | −0.0061 | −0.1573 | 0.0711 | 0.0705 |
| Ser | −0.0043 | 0.0004 | −0.0297 | 0.0429 | 0.0543 | −0.0064 | −0.0037 |
| Pro | 0.0151 | 0.0056 | 0.0117 | −0.0474 | −0.0504 | −0.0056 | −0.1171 |
| Val | 0.0118 | −0.0136 | −0.0175 | −0.0390 | 0.1017 | 0.0007 | 0.1844 |
| Leu/Ile | 0.0077 | −0.0222 | 0.0278 | −0.0473 | 0.1310 | −0.0311 | 0.2073 |
| Met | 0.0005 | 0.0022 | −0.0099 | −0.0110 | −0.0263 | −0.0011 | 0.1636 |
| His | 0.0127 | 0.0268 | 0.0211 | −0.0210 | −0.0078 | −0.0241 | 0.0796 |
| Phe | −0.0061 | −0.0067 | 0.0590 | −0.0062 | 0.0043 | −0.0030 | 0.3788 |
| Tyr | 0.0024 | −0.0004 | 0.0207 | 0.0109 | −0.0632 | 0.0329 | 0.3731 |
| Asx | 0.0128 | 0.0221 | 0.0270 | 0.0155 | −0.0243 | −0.0654 | 0.0080 |
| Glx | −0.0165 | 0.0353 | 0.0105 | 0.0545 | −0.0122 | 0.0307 | −0.0371 |
| Orn | −0.0283 | −0.0037 | −0.0018 | 0.0774 | −0.0132 | 0.0543 | −0.0122 |
| Cit | −0.0245 | −0.0369 | 0.0948 | −0.0275 | 0.0267 | 0.0172 | −0.1267 |
| Arg | 0.0143 | −0.0267 | 0.0038 | −0.0852 | 0.0238 | −0.0760 | −0.0238 |
| C2 | −0.0383 | −0.0190 | −0.0662 | −0.0032 | 0.1821 | 0.0498 | −0.0464 |
| C3 | −0.0393 | −0.0062 | −0.0633 | 0.0429 | −0.0120 | −0.0245 | −0.0264 |
| C4/C14 | −0.0289 | 0.0019 | −0.0123 | −0.0138 | 0.0184 | −0.0493 | −0.1161 |
| C5:1 | −0.0084 | 0.0076 | 0.0132 | 0.0108 | −0.0282 | −0.0486 | −0.0195 |
| C5's | 0.0226 | 0.0034 | 0.0270 | −0.0227 | 0.0013 | −0.1253 | −0.0287 |
| C4-OH | −0.0469 | −0.0060 | −0.0359 | −0.0361 | 0.2157 | 0.0747 | −0.0091 |
| C5-OH/C3-DC | −0.0082 | −0.0058 | −0.0130 | −0.0062 | 0.0187 | 0.0036 | −0.0661 |
| Ci4-DC/C4-DC | −0.0587 | −0.0321 | 0.1657 | 0.0678 | 0.0156 | 0.0074 | 0.0355 |
| C8:1 | −0.0387 | −0.0177 | −0.0844 | −0.0085 | 0.0234 | 0.3548 | −0.0194 |
| C8 | 0.2219 | −0.0274 | −0.0498 | −0.0805 | −0.0734 | −0.000014 | −0.0395 |
| C5-DC | −0.0009 | −0.0319 | 0.2871 | 0.0046 | −0.0007 | −0.1802 | 0.0263 |
| C6-DC | −0.0290 | −0.0157 | 0.2638 | 0.0164 | 0.0206 | −0.2015 | 0.0092 |
| C10:3 | −0.0297 | −0.0115 | −0.0537 | −0.0047 | −0.0020 | 0.3438 | 0.0001 |
| C10:2 | −0.0071 | −0.0234 | −0.0372 | −0.00010 | −0.0290 | 0.2986 | 0.0467 |
| C10:1 | 0.0831 | −0.0178 | −0.0787 | −0.0383 | −0.0263 | 0.2167 | 0.0164 |
| C10 | 0.2150 | −0.0288 | −0.0137 | −0.0730 | −0.0725 | −0.0109 | −0.0274 |
| C10-OH/C8-DC | −0.0148 | 0.0362 | 0.1147 | −0.0154 | 0.0233 | −0.0266 | 0.0666 |
| C12:1 | 0.0666 | 0.0073 | −0.0412 | −0.0452 | 0.0107 | 0.1193 | 0.0378 |
| C12 | 0.1771 | −0.0104 | 0.0360 | −0.0487 | −0.0578 | −0.0667 | 0.0026 |
| C12-OH/C10-DC | −0.0260 | 0.0894 | 0.1022 | −0.0023 | −0.0115 | −0.0351 | 0.0481 |
| C14:2 | 0.0829 | −0.0202 | −0.0255 | −0.0121 | 0.0383 | 0.0522 | 0.0426 |
| C14:1 | 0.1244 | −0.0078 | −0.0250 | −0.0155 | 0.0195 | −0.0316 | 0.0090 |
| C14 | 0.1525 | −0.0039 | 0.0116 | 0.0087 | −0.0506 | −0.1014 | −0.0003 |
| C14:1-OH/C12:1-DC | −0.0180 | 0.0310 | 0.0281 | 0.0249 | 0.0363 | 0.0146 | 0.0719 |
| C14-OH/C12-DC | −0.0334 | 0.0759 | 0.0005 | 0.0176 | 0.0111 | 0.0233 | 0.0450 |
| C16 | −0.0012 | −0.0152 | 0.0178 | 0.1996 | −0.0165 | −0.0673 | 0.0014 |
| C16-OH/C14-DC | −0.0182 | 0.1759 | −0.0277 | −0.0213 | −0.0269 | −0.0157 | −0.0277 |

TABLE 2A-continued

Scoring coefficients for metabolite factors 1-7.

| Metabolite | Factor 1 | Factor 2 | Factor 3 | Factor 4 | Factor 5 | Factor 6 | Factor 7 |
|---|---|---|---|---|---|---|---|
| C18:2 | −0.0368 | −0.0343 | −0.0034 | 0.2265 | −0.0190 | 0.0774 | 0.0127 |
| C18:1 | −0.0367 | −0.0211 | 0.0319 | 0.2375 | −0.0088 | −0.0240 | −0.0097 |
| C18 | −0.0282 | −0.0185 | 0.0217 | 0.2371 | −0.0336 | −0.0527 | −0.0607 |
| C18:1-OH/C16:1-DC | −0.0193 | 0.1413 | −0.0260 | −0.0067 | 0.0268 | −0.0237 | −0.0073 |
| C18-OH/C16-DC | −0.0126 | 0.2216 | −0.0306 | −0.0371 | −0.0458 | −0.0228 | −0.0242 |
| C20 | −0.0120 | 0.1115 | −0.0159 | 0.0360 | −0.0165 | −0.0371 | −0.0409 |
| C20:1-OH/C18:1-DC | −0.0161 | 0.2219 | −0.0207 | −0.0417 | −0.0280 | −0.0230 | −0.0036 |
| C20-OH/C18-DC | −0.0110 | 0.2359 | −0.0406 | −0.0450 | −0.0535 | −0.0108 | −0.0313 |
| C22 | −0.0008 | −0.0154 | −0.0095 | 0.0509 | −0.0235 | 0.0386 | −0.0157 |
| C6:1-DC/C8:1-OH | −0.0104 | −0.0328 | 0.1936 | 0.0080 | −0.0101 | 0.0013 | 0.0263 |
| C8:1-DC | −0.0144 | −0.0080 | 0.1981 | 0.0056 | −0.0138 | −0.0205 | 0.0498 |
| C16:2 | 0.1467 | −0.0330 | −0.0398 | −0.0131 | −0.0025 | −0.0150 | −0.0081 |
| C16:1 | 0.1318 | −0.0183 | −0.0186 | 0.0260 | −0.0153 | −0.0713 | −0.0162 |
| C16:1-OH/C14:1-DC | −0.0139 | 0.0275 | 0.0076 | 0.0701 | 0.0379 | −0.0701 | −0.0009 |
| C18:2-OH | −0.0371 | 0.0224 | 0.0250 | 0.0507 | 0.0484 | −0.0261 | 0.0157 |
| C20:4 | −0.0485 | −0.0203 | −0.0011 | 0.2130 | −0.0523 | 0.0130 | −0.0187 |
| HBUT | −0.0219 | −0.0292 | 0.0257 | −0.0411 | 0.2727 | −0.0383 | 0.0096 |
| KET | −0.0221 | −0.0271 | 0.0271 | −0.0450 | 0.2786 | −0.0384 | 0.0114 |
| NEFA | 0.0064 | −0.0390 | −0.0022 | −0.0171 | 0.0291 | 0.0024 | −0.0456 |

TABLE 2B

Scoring coefficients for metabolite factors 8-14.

| Metabolite | Factor 8 | Factor 9 | Factor 10 | Factor 11 | Factor 12 | Factor 13 | Factor 14 |
|---|---|---|---|---|---|---|---|
| Gly | 0.3310 | −0.0535 | 0.0346 | −0.0677 | −0.0095 | −0.0481 | −0.0507 |
| Ala | 0.0421 | −0.0441 | 0.0710 | 0.0117 | −0.0571 | 0.3342 | −0.1261 |
| Ser | 0.2606 | −0.0558 | −0.0728 | 0.0121 | 0.1069 | −0.2145 | −0.0480 |
| Pro | 0.1472 | 0.0287 | 0.0314 | 0.2272 | 0.1529 | 0.3344 | −0.1155 |
| Val | 0.0218 | 0.0021 | 0.0431 | −0.1278 | 0.2450 | −0.0174 | 0.1993 |
| Leu/Ile | 0.0503 | −0.0131 | 0.0431 | −0.1152 | 0.2371 | −0.0290 | 0.1646 |
| Met | 0.2040 | −0.0616 | 0.1335 | −0.1286 | −0.2548 | 0.0034 | 0.0727 |
| His | 0.0418 | −0.0408 | −0.1547 | 0.3355 | 0.1131 | −0.1258 | −0.0696 |
| Phe | −0.1045 | −0.0384 | −0.0625 | 0.0278 | −0.1147 | −0.1117 | −0.0619 |
| Tyr | −0.0535 | −0.1113 | −0.0563 | −0.0023 | −0.2070 | −0.0242 | −0.0796 |
| Asx | 0.0202 | −0.1111 | 0.4358 | −0.1012 | 0.0604 | 0.1039 | −0.1405 |
| Glx | −0.0576 | −0.0016 | −0.0017 | 0.0568 | 0.4552 | 0.1332 | −0.1057 |
| Orn | 0.1679 | 0.0020 | −0.0890 | 0.0459 | 0.1394 | 0.0048 | −0.0479 |
| Cit | 0.1494 | 0.0449 | −0.0866 | 0.3038 | 0.0592 | 0.0710 | 0.0115 |
| Arg | 0.1783 | 0.0466 | 0.0397 | 0.3132 | −0.1845 | 0.0291 | 0.1650 |
| C2 | 0.0079 | 0.1957 | 0.0106 | 0.0103 | −0.0384 | −0.0094 | −0.0579 |
| C3 | −0.0460 | 0.3793 | 0.0754 | −0.0139 | −0.0875 | −0.0198 | 0.0716 |
| C4/C14 | −0.0336 | 0.4473 | −0.0690 | 0.0237 | −0.0175 | 0.0057 | −0.0929 |
| C5:1 | 0.1662 | 0.0480 | −0.2090 | −0.3301 | −0.0678 | 0.1566 | −0.0496 |
| C5's | −0.0441 | 0.3654 | −0.0896 | −0.0164 | 0.0529 | −0.0413 | 0.0040 |
| C4-OH | 0.0242 | 0.0631 | 0.0042 | −0.0048 | 0.0208 | 0.0165 | −0.0849 |
| C5-OH/C3-DC | −0.0216 | 0.0521 | 0.4659 | 0.0130 | −0.0742 | −0.0509 | −0.0083 |
| Ci4-DC/C4-DC | −0.0064 | 0.0110 | −0.0337 | −0.0802 | −0.0272 | −0.0432 | 0.0784 |
| C8:1 | 0.0373 | −0.0140 | −0.1275 | −0.0956 | 0.1208 | 0.0619 | −0.0057 |
| C8 | 0.0266 | 0.0108 | 0.0359 | −0.0911 | 0.1318 | −0.1091 | 0.0552 |
| C5-DC | −0.0333 | −0.0141 | −0.0079 | 0.0518 | 0.0527 | −0.0231 | −0.0161 |
| C6-DC | −0.0502 | −0.0158 | 0.0492 | 0.0875 | 0.0444 | 0.0656 | −0.1168 |
| C10:3 | −0.0072 | −0.0901 | 0.0607 | 0.0005 | 0.0497 | −0.0052 | 0.0387 |
| C10:2 | −0.0302 | −0.0696 | −0.0176 | 0.0184 | −0.0360 | −0.0406 | 0.0785 |
| C10:1 | 0.0043 | −0.0407 | 0.1519 | 0.0076 | −0.0541 | −0.0753 | −0.0078 |
| C10 | 0.0147 | −0.0235 | 0.0748 | −0.0504 | 0.1208 | −0.1416 | 0.0479 |
| C10-OH/C8-DC | 0.0195 | 0.0111 | −0.0687 | −0.1080 | −0.1074 | 0.0108 | −0.0927 |
| C12:1 | 0.0288 | −0.0146 | −0.0055 | −0.0300 | −0.0914 | 0.0408 | −0.1190 |
| C12 | 0.0090 | −0.0057 | −0.0060 | −0.0862 | 0.0529 | −0.0582 | 0.1179 |
| C12-OH/C10-DC | −0.0202 | −0.0136 | 0.0351 | −0.0396 | −0.0914 | 0.0016 | −0.0187 |
| C14:2 | 0.0073 | −0.0444 | −0.0451 | 0.0599 | −0.0743 | 0.0499 | −0.0243 |
| C14:1 | −0.0090 | −0.0082 | −0.0234 | 0.0607 | −0.0149 | 0.0405 | −0.0557 |
| C14 | −0.0414 | 0.0196 | −0.0951 | 0.0089 | 0.0770 | 0.0282 | 0.0198 |
| C14:1-OH/C12:1-DC | −0.0246 | 0.0334 | −0.0753 | 0.0630 | −0.1797 | 0.0580 | −0.0882 |
| C14-OH/C12-DC | −0.0290 | 0.0514 | −0.0600 | 0.0225 | −0.1297 | 0.0418 | 0.1051 |
| C16 | −0.0526 | 0.0345 | 0.0232 | −0.0665 | 0.0291 | 0.0270 | −0.0067 |
| C16-OH/C14-DC | −0.0129 | 0.0094 | 0.0387 | −0.0114 | 0.0452 | 0.0220 | −0.0086 |
| C18:2 | 0.0304 | −0.0812 | −0.0248 | −0.0525 | 0.0015 | −0.0062 | −0.0200 |
| C18:1 | −0.0007 | −0.0289 | −0.0137 | −0.0314 | 0.0140 | −0.0131 | −0.0579 |
| C18 | −0.0068 | 0.0378 | −0.0078 | −0.0166 | 0.0556 | −0.1022 | 0.1252 |
| C18:1-OH/C16:1-DC | 0.0125 | −0.0231 | 0.0342 | 0.0274 | −0.0324 | 0.0667 | −0.0518 |
| C18-OH/C16-DC | 0.0006 | −0.0106 | −0.0077 | −0.0305 | 0.1301 | −0.0774 | 0.0022 |

TABLE 2B-continued

Scoring coefficients for metabolite factors 8-14.

| Metabolite | Factor 8 | Factor 9 | Factor 10 | Factor 11 | Factor 12 | Factor 13 | Factor 14 |
|---|---|---|---|---|---|---|---|
| C20 | 0.0080 | −0.0003 | 0.0532 | 0.0940 | −0.0507 | −0.0010 | 0.0674 |
| C20:1-OH/C18:1-DC | −0.0043 | −0.0108 | −0.0217 | 0.0046 | 0.0809 | −0.0865 | −0.1107 |
| C20-OH/C18-DC | 0.0013 | −0.0034 | −0.0198 | −0.0176 | 0.1540 | −0.1071 | −0.0966 |
| C22 | −0.0296 | −0.0140 | −0.0887 | 0.0486 | −0.0352 | 0.0558 | 0.7219 |
| C6:1-DC/C8:1-OH | −0.0230 | −0.0640 | 0.0439 | 0.0273 | 0.0196 | −0.0341 | 0.0563 |
| C8:1-DC | −0.0118 | −0.0662 | −0.0308 | −0.0322 | −0.0168 | −0.0327 | 0.0723 |
| C16:2 | 0.0099 | −0.0551 | 0.0250 | 0.0511 | 0.0015 | 0.0587 | 0.0558 |
| C16:1 | −0.0128 | −0.0231 | 0.0266 | 0.0213 | 0.0049 | 0.0806 | −0.0244 |
| C16:1-OH/C14:1-DC | −0.0119 | 0.0297 | 0.0785 | 0.0588 | −0.1504 | 0.1155 | −0.0184 |
| C18:2-OH | −0.0611 | −0.0102 | −0.0529 | 0.3062 | −0.0793 | 0.0461 | 0.1112 |
| C20:4 | −0.0070 | −0.0018 | 0.0259 | −0.0209 | 0.0100 | −0.0357 | 0.1083 |
| HBUT | 0.0332 | −0.0767 | 0.0140 | 0.0301 | 0.1007 | 0.0012 | 0.0381 |
| KET | 0.0310 | −0.0708 | 0.0123 | 0.0201 | 0.1149 | −0.0166 | 0.0399 |
| NEFA | −0.0700 | −0.0214 | 0.0056 | −0.0538 | 0.0918 | 0.5377 | 0.1184 |

4. Determining the Level of a Biomarker

The presence or level of the biomarker in a sample may be determined or detected by any method known by one of skill in the art. For example, the biomarker may be detected and/or quantified by employing mass spectroscopy (including, for example, tandem flow injection MS/MS), colorimetric or fluorimetric assay, chromatography such as gas or liquid chromatography, MALDI-TOF, or a combination thereof. In some embodiments, the biomarker is detected with LC-MS. In some embodiments, the biomarker is detected with GC-MS.

5. Methods a. Methods for Assessing the Risk of Death or MACE

Provided herein is a method of assessing the risk of death or MACE in a subject diagnosed with HFpEF. The method may include determining in a sample from the subject the level of each metabolite in at least one factor, and comparing the level of each metabolite in the sample to a standard. The level of the metabolite in the subject relative to a standard may be indicative of the risk of death or MACE in the subject. In some embodiments, the method may further include determining that the subject has a risk of death or MACE when the level of each metabolite in the subject is different from the standard. In some embodiments, the factor is selected from the group consisting of factor 1, factor 3, factor 4, factor 5, factor 10, factor 12, and factor 14. In some embodiments, the level of each metabolite in more than one factor is determined. In some embodiments, the level of each metabolite in two factors is determined. In some embodiments, the level of each metabolite in three factors is determined. In some embodiments, the level of each metabolite in four factors is determined. In some embodiments, the level of each metabolite in five factors is determined. In some embodiments, the level of each metabolite in six factors is determined. In some embodiments, the level of each metabolite in seven factors is determined.

In other embodiments, the method may include determining in a sample from the subject the level of each metabolite in at least one factor, calculating a weighted level of each metabolite by multiplying the determined level by a scoring coefficient specific for each metabolite, adding the weighted level of each metabolite in the factor together to yield a factor score, comparing the factor score of the sample to a non-HFpEF standard, and determining that the subject has an increased risk of death or MACE when the factor score in the subject is different from the standard. In some embodiments, the factor is selected from the group consisting of factor 1, factor 3, factor 4, factor 5, factor 10, factor 12, and factor 14. In some embodiments, the level of each metabolite in more than one factor is determined. In some embodiments, the level of each metabolite in two factors is determined. In some embodiments, the level of each metabolite in three factors is determined. In some embodiments, the level of each metabolite in four factors is determined. In some embodiments, the level of each metabolite in five factors is determined. In some embodiments, the level of each metabolite in six factors is determined. In some embodiments, the level of each metabolite in seven factors is determined.

b. Method of Developing a Treatment Plan for a Subject

Provided herein is a method of developing a treatment plan for a subject. The method may include determining in a sample from the subject the level of each metabolite in at least one factor, comparing the level of each metabolite in the sample to a standard, determining that the subject has a greater probability of having HFpEF or HFrEF, or having a risk of death or MACE when the level of each metabolite in the subject is different from the standard, and developing a treatment plan based on the risk of cardiovascular disease in the subject. The level of the metabolite in the subject relative to a standard may be indicative of the risk of heart failure, or risk of death or MACE in the subject. In some embodiments, the method may further include determining that the subject has a risk of death or MACE when the level of each metabolite in the subject is different from the standard. In some embodiments, the factor is selected from the group consisting of factor 1, factor 3, factor 4, factor 5, factor 10, factor 12, and factor 14. In some embodiments, the level of each metabolite in more than one factor is determined. In some embodiments, the level of each metabolite in two factors is determined. In some embodiments, the level of each metabolite in three factors is determined. In some embodiments, the level of each metabolite in four factors is determined. In some embodiments, the level of each metabolite in five factors is determined. In some embodiments, the level of each metabolite in six factors is determined. In some embodiments, the level of each metabolite in seven factors is determined. In some embodiments, the treatment plan includes administering a treatment for heart failure.

c. Method for Diagnosing Heart Failure with Preserved Ejection Fraction

Provided herein is a method of diagnosing HFpEF. The method may include determining in a sample from the subject the level of each metabolite in at least one factor, and comparing the level of each metabolite in the sample to a standard. The level of the metabolite in the subject relative to a standard may be indicative of the risk of death or MACE in the subject. The method may further include identifying the subject as having HFpEF when the level of each metabolite in the subject is different from the standard. In some embodiments, the method may further include determining that the subject has a risk of death or MACE when the level of each metabolite in the subject is different from the standard. In some embodiments, the factor is selected from the group consisting of factor 1, factor 3, factor 4, factor 5, factor 10, factor 12, and factor 14. In some embodiments, the level of each metabolite in more than one factor is determined. In some embodiments, the level of each metabolite in two factors is determined. In some embodiments, the level of each metabolite in three factors is determined. In some embodiments, the level of each metabolite in four factors is determined. In some embodiments, the level of each metabolite in five factors is determined. In some embodiments, the level of each metabolite in six factors is determined. In some embodiments, the level of each metabolite in seven factors is determined. In some embodiments, the factor is factor 4.

6. Standard

The standard may be a predetermined value or range, which is employed as a benchmark against which to assess the measured result. The terms "standard," "reference level," "reference," and "control" are used herein interchangeably. The predetermined level may be from a subject or a group. "Control group" as used herein refers to a group of control subjects. A control subject may be a healthy or normal subject or a subject having no clinical signs or symptoms of heart failure and/or having a normal left ventricular ejection fraction. A control subject may be a healthy or normal subject or a subject having no clinical signs or symptoms of cardiovascular disease. The predetermined level may be a cutoff value from a control group. The predetermined level may be an average from a control group.

The amount or concentration of a biomarker may be "unchanged," "favorable" (or "favorably altered"), or "unfavorable" (or "unfavorably altered"). "Elevated" or "increased" refers to an amount or a concentration in a test sample that is greater than a standard. The term "lowered" or "reduced" refers to an amount or a concentration in a test sample that is less than a standard. The term "altered" refers to an amount or a concentration in a sample that is altered (increased or decreased) over a standard.

Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having the disease. A description of ROC analysis as applied according to the present disclosure is provided in P. J. Heagerty et al. (Time-dependent ROC curves for censored survival data and a diagnostic marker, Biometrics 2000, 56, 337-44), the disclosure of which is hereby incorporated by reference in its entirety.

Alternatively, cutoff values can be determined by a quartile analysis of biological samples of a patient group. For example, a cutoff value can be determined by selecting a value that corresponds to any value in the 25th-75th percentile range, preferably a value that corresponds to the 25th percentile, the 50th percentile or the 75th percentile, and more preferably the 75th percentile.

Such statistical analyses can be performed using any method known in the art and can be implemented through any number of commercially available software packages (e.g., from Analyse-it Software Ltd., Leeds, UK; StataCorp LP, College Station, Tex.; SAS Institute Inc., Cary, N.C.).

The healthy or normal levels or ranges for a biomarker are defined in accordance with standard practice.

7. Examples

EXAMPLE 1

Metabolomic Profiling Identifies Biomarkers of Mitochondrial Function in Heart Failure with Preserved Versus Reduced Ejection Fraction The plasma metabolite signature of cross-sectional HFpEF was determined. Abnormalities were identified in fatty acid, amino acid, and carbohydrate metabolism in patients with HFpEF.

The subjects included patients who were presenting for cardiac catheterization at Duke University Medical Center between 2004 and 2010 and enrolled in the CATHGEN biorepository. From these CATHGEN subjects, HFpEF cases, HFrEF controls, and controls without heart failure or diastolic dysfunction (no-HF controls) were identified. HFpEF cases were defined by left ventricular ejection fraction (LVEF) ≥45%, diastolic dysfunction grade ≥1, and history of HF. HFrEF controls were defined in the same manner as HFpEF cases, except for having LVEF <45%. No-HF controls were defined by LVEF ≥45%, normal diastolic function, and no history of heart failure. Patients were excluded from analysis if they had a history of congenital heart disease, moderate-severe valvular disease on echocardiography, cardiac transplantation, or end-stage renal disease.

Fasting whole blood and plasma samples were collected from each patient in EDTA tubes via femoral artery sheath prior to cardiac catheterization. 69 metabolites in the samples were analyzed with targeted, quantitative mass spectrometry-based measurements.

Results were analyzed with multidimensional dataset reduction with Principal Components Analysis (PCA). ANCOVA was used to assess difference in PCA derived metabolite factor levels across groups. Adjustments were made for age, race, sex, extent of CAD, hypertension, dyslipidemia, BMI, DM, baseline eGFR, and batch. Statistical significance was defined by Bonferroni correction at total number of factors. Post-hoc pairwise comparisons were used to understand the relationship of HFpEF to each control group for each metabolite factor significant in omnibus ANCOVA.

Limitations to the study include that the study sample was not population-based but instead was composed of individuals referred for cardiac catheterization. However, a significant portion of each group lacked coronary disease. Despite careful adjustment for important clinical covariates and strict consistency in sample collection, other measured and unmeasured variables may have influenced these results. Inter-individual variability in metabolite profiles due to many demographic and clinical factors are presently unknown but thoroughly adjusted for in this study.

In the basic model, omnibus ANCOVA identified two metabolite factors significant at the Bonferroni corrected significance threshold ($P<0.0036$); both were composed of acylcarnitines of varying chain length (TABLE 4). In the fully adjusted model, the long-chain acylcarnitine factor (LCAC) remained statistically significant ($P<0.0001$) at the Bonferroni-corrected significance threshold. Mean levels of the LCAC factor were significantly greater in HFrEF controls than HFpEF cases (least square means±standard deviation: 0.504±0.161 vs. 0.131±0.162; P=0.0004). Both HFrEF and HFpEF LCAC factor levels were significantly greater than no-HF controls (−0.245±0.173; P<0.0001 and P=0.003 for comparisons with HFrEF and HFpEF, respectively). Results are shown in TABLES 3-4.

TABLE 3

Baseline patient characteristics.

|  | HFpEF (N = 282) | HFrEF (N = 279) | No-HF (N = 191) |
|---|---|---|---|
| Age, years | 66 (12) | 61 (13) | 55 (13) |
| Gender, Male | 58% | 70% | 61% |
| BMI, kg/m$^2$ | 31 (7) | 29 (8) | 30 (7) |
| Race |  |  |  |
| Caucasian | 70% | 66% | 80% |
| African-American | 27% | 30% | 17% |
| Hispanic | 1% | 3% | 1% |
| Other | 2% | 1% | 2% |
| Ejection Fraction (LVEF), % | 58 (8) | 28 (9) | 58 (7) |

TABLE 3-continued

Baseline patient characteristics.

|  | HFpEF (N = 282) | HFrEF (N = 279) | No-HF (N = 191) |
|---|---|---|---|
| GFR, mL/min/1.73 m$^2$ | 64 (25) | 66 (23) | 84 (23) |
| Hypertension | 75% | 67% | 56% |
| Diabetes Mellitus | 39% | 37% | 18% |
| Diseased Coronary Vessels* |  |  |  |
| 0 | 43% | 33% | 45% |
| 1 | 19% | 16% | 22% |
| 2 | 15% | 14% | 17% |
| 3 | 23% | 38% | 16% |
| Dyslipidemia | 60% | 58% | 52% |
| Smoking | 48% | 51% | 41% |

Values are % or mean ± standard deviation.
*Coronary vessel diseased if stenosed >75% when visualized on coronary angiography.
Abbreviations:
HFpEF indicates heart failure with preserved ejection fraction;
HFrEF, heart failure with reduced ejection fraction;
BMI, body mass index;
EF, ejection fraction;
GFR, estimated glomerular filtration rate.

TABLE 4

Adjusted comparisons of PCA-derived metabolite factor levels between HFpEF, HFrEF, and no heart failure controls.*

|  |  | ANCOVA* | | Pairwise Comparisons§ | | | Metabolite Factor Means Values¶ | | |
|---|---|---|---|---|---|---|---|---|---|
| Factor | Description | Basic† | Fully Adjusted‡ | HFpEF vs HFrEF | HFpEF vs No-HF | HFrEF vs No-HF | HFpEF (N = 263) | HFrEF (N = 273) | No-HF (N = 180) |
| 1 | Medium-chain acylcarnitines | 0.04 | 0.13 |  |  |  |  |  |  |
| 2 | Long-chain dicarboxyl-acylcarnitines | 0.008 | 0.04 | 0.05 | 1.00 | 0.30 | 0.084 (0.178) | 0.339 (0.176) | 0.136 (0.190) |
| 3 | Short-chain dicarboxyl-acylcarnitines | 0.005 | 0.07 |  |  |  |  |  |  |
| 4 | Long-chain acylcarnitines | <0.0001 | <0.0001 | 0.0004 | 0.003 | <0.0001 | 0.131 (0.162) | 0.504 (0.161) | −0.245 (0.173) |
| 5 | Ketones and related metabolites | 0.13 | 0.15 |  |  |  |  |  |  |
| 6 | C8-C10 acylcarnitines | 0.0001 | 0.09 |  |  |  |  |  |  |
| 7 | BCAA and related metabolites | 0.04 | 0.005 | 0.03 | 1.00 | 0.01 | −0.187 (0.150) | 0.041 (0.148) | −0.254 (0.160) |
| 8 | Various amino acids | 0.14 | 0.07 |  |  |  |  |  |  |
| 9 | Short-chain acylcarnitines | 0.13 | 0.95 |  |  |  |  |  |  |
| 10 | Asparagine, aspartate, 3-hydroxyisovaleryl/malonyl carnitine | 0.17 | 0.11 |  |  |  |  |  |  |
| 11 | Histidine, arginine, tigylcarnitine, 3-hydroxylinoleyl/hexadecadienedioyl carnitine | 0.11 | 0.01 | 1.00 | 0.05 | 0.001 | −0.320 (0.112) | −0.352 (0.111) | −0.132 (0.119) |
| 12 | Valine, glutamine, glutamate | 0.008 | 0.004 | 0.03 | 1.00 | 0.008 | −0.217 (0.152) | −0.447 (0.151) | −0.134 (0.162) |
| 13 | Alanine, proline, free fatty acids | 0.02 | 0.03 | 0.40 | 0.60 | 0.02 | −0.006 (0.141) | 0.125 (0.140) | −0.133 (0.151) |

TABLE 4-continued

Adjusted comparisons of PCA-derived metabolite factor levels
between HFpEF, HFrEF, and no heart failure controls.*

|  |  | ANCOVA* | | Pairwise Comparisons§ | | | Metabolite Factor Means Values¶ | | |
|---|---|---|---|---|---|---|---|---|---|
| Factor | Description | Basic† | Fully Adjusted‡ | HFpEF vs HFrEF | HFpEF vs No-HF | HFrEF vs No-HF | HFpEF (N = 263) | HFrEF (N = 273) | No-HF (N = 180) |
| 14 | Docosanoyl-carnitine | 0.004 | 0.03 | 1.00 | 0.20 | 0.03 | 0.68 (0.137) | 0.003 (0.135) | 0.247 (0.145) |

*Statistical significance in omnibus ANCOVA analyses was P < 0.0036, reflecting Bonferroni correction for 14 factor comparisons.
†P values for basic model, adjusted for age, race and sex.
‡P values for full model, adjusted for age, race, sex, body mass index, number of diseased coronary arteries, history of diabetes, hypertension, dyslipidemia, smoking, and glomerular filtration rate.
§Pairwise comparisons for factors significant at Bonferroni corrected threshold test for significant between-group differences. P values for factors significant at nominal threshold of P < 0.05 are reported for exploratory purposes. P values reflect between-group pairwise contrasts generated from the fully adjusted ANCOVA procedure.
¶Values are least square means, adjusted for all 10 covariates. Standard error of the mean is provided beneath each value.
Abbreviations:
HFpEF indicates heart failure with preserved ejection fraction;
HFrEF, heart failure with reduced ejection fraction;
HF, heart failure;
ANCOVA, analysis of covariance;
BCAA, branched-chain amino acids;
C, carbon chain length.

Biochemically, LCAC are intermediates in the fatty acid ß-oxidation pathway. Structurally, they are long-chain fatty acids (LCFA) esterified to carnitine. Functionally, they facilitate transfer of LCFAs into the mitochondria for ß-oxidation. Although typically short-lived, LCAC accumulate in states of inefficient fatty acid oxidation (FAO), which may be due to (a) defects in mitochondrial FAO enzymes or (b) increased FAO relative to tricarboxylic acid (TCA) flux. This leads to a bottleneck of carbon substrates at the TCA cycle. Altogether, the plasma LCAC elevations in HFpEF and HFrEF observed highlighted a shared metabolic impairment characteristic of the heart failure state and could serve as biomarkers for discriminating HFpEF from HFrEF and patients without heart failure.

EXAMPLE 2

Metabolomic Profiling Identifies Biomarkers Predicting Adverse Outcomes in Patients with Heart Failure with Preserved Ejection Fraction Targeted metabolomic profiling was used to identify metabolites in peripheral blood that are independently associated with survival or major adverse cardiac events in patients with HFpEF.

The subjects included patients who underwent cardiac catheterization at Duke University Medical Center between 2004-2010 who were subsequently enrolled in the CATH-GEN biorepository. HFpEF subjects were defined as LVEF ≥50%, had NYHA class II-IV symptoms, and demonstrated one of the following within 12 months prior to sample collection: elevated NT-proBNP (>400 pg/mL), loop diuretic use, or HF ICD-9 code associated at any clinical encounter. Subjects were excluded from the study if the subject had a history of congenital heart disease, significant valvular disease, cardiac transplantation, end-stage renal disease, or if there was any significant cardiac event (MI, CABG, PTCA) within the one month prior to catheterization.

Fasting whole blood and plasma samples were collected from each patient in EDTA tubes via femoral artery sheath. 69 metabolites in the samples were analyzed with targeted, quantitative mass spectrometry-based measurements.

Results were analyzed with multidimensional dataset reduction with Principal Components Analysis (PCA). Multivariate time-to-event analyses using Cox proportional hazard modeling was used to determine associations between metabolite factor levels and clinical endpoints of (1) all-cause mortality or (2) all-cause mortality or major adverse cardiac event (myocardial infarction, coronary artery bypass grafting, or percutaneous coronary intervention).

Limitations to the study include that the study sample was not population-based but instead was composed of individuals referred for cardiac catheterization. However, a significant portion of each group lacked coronary disease. Despite careful adjustment for important clinical covariates and strict consistency in sample collection, other measured and unmeasured variables may have influenced these results. Inter-individual variability in metabolite profiles due to many demographic and clinical factors are presently unknown but thoroughly adjusted for in this study.

Multivariate adjusted time-to-event analysis demonstrated that six of 14 PCA-derived factors were independently associated with either (1) time to all-cause mortality or (2) time to all-cause mortality or MACE. Higher levels of 4 metabolite factors were associated with increased risk of adverse outcomes: medium-chain acylcarnitines (hazard ratio [HR] for death 2.47 [95% CI, 1.67-3.64], P<0.001), short-chain dicarboxylacylcarnitines (HR for death 1.44 [95% CI, 1.13-1.84], P=0.04), 3-Hydroxy-Linoleylcarnitine (HR for death 1.66 [95% CI, 1.31-2.10], P<0.001), and ketone related metabolites (HR for death or MACE 1.36 [95% CI, 1.07-1.74], P=0.01). Higher levels of 2 metabolites were associated with decreased risk of adverse outcomes: factor composed of glycine, ornithine, and tiglyl-carnitine (HR for death or MACE 0.72 [95% CI, 0.53-0.99], P=0.04), and docosanoylcarnitine (HR 0.71, [95% CI, 0.51-0.99], P=0.049). Results are shown in TABLES 5-6.

TABLE 5

Baseline patient characteristics.

| | HFpEF (n = 131) |
|---|---|
| Age, years | 68 ± 9 |
| Female, % | 48 |
| Race | |
| Caucasian, % | 76 |
| African American, % | 20 |
| BMI, kg/m$^2$ | 32 ± 8 |
| Ejection Fraction, % | 60 ± 8 |
| Hypertension, % | 69 |
| Diabetes Mellitus, % | 36 |
| Hyperlipidemia*, % | 52 |
| COPD, % | 9 |
| Previous smoking, % | 48 |
| Diseased Coronary Vessels† | |
| 0 | 52 |
| 1 | 17 |
| 2 | 12 |
| 3 | 19 |

*Values are percentages or mean ± standard deviation.

TABLE 6

Multivariable association of metabolite factors with death or MACE.*

| | Death | | Death or MACE | |
|---|---|---|---|---|
| Factor | HR (95% CI) | P | HR (95% CI) | P |
| 1 Medium-chain acylcarnitines | 2.47 (1.67-3.64) | <0.001 | 2.32 (1.62-3.31) | 0.001 |
| 2 Long-chain dicarboxylacylcarnitines | 1.12 (0.99-1.27) | 0.07 | 1.12 (0.98-1.26) | 0.09 |
| 3 Short-chain dicarboxylacylcarnitines | 1.44 (1.13-1.84) | 0.04 | 1.33 (1.05-1.70) | 0.02 |
| 4 Long-chain acylcarnitines | 0.81 (0.59-1.09) | 0.16 | 0.80 (0.59-1.07) | 0.13 |
| 5 Ketone related | 1.25 (1.00-1.58) | 0.051 | 1.36 (1.07-1.74) | 0.01 |
| 6 Branched-chain amino acids | 1.12 (0.81-1.54) | 0.51 | 1.12 (0.82-1.52) | 0.48 |
| 7 C8-C10 Acylcarnitines | 1.14 (0.90-1.43) | 0.28 | 1.10 (0.87-1.38) | 0.43 |
| 8 Urea cycle amino acids | 0.74 (0.48-1.14) | 0.17 | 0.73 (0.47-1.12) | 0.15 |
| 9 Short-chain acylcarnitines | 1.08 (0.85-1.36) | 0.55 | 0.96 (0.76-1.23) | 0.77 |
| 10 Glycine, Ornithine, Tiglyl-carnitine | 0.75 (0.54-1.03) | 0.07 | 0.72 (0.53-0.99) | 0.04 |
| 11 Asparagine, Aspartate, Malonyl-carnitine | 1.33 (0.87-2.02) | 0.19 | 1.31 (0.88-1.95) | 0.19 |
| 12 3-Hydroxy-linoleyl-carnitine | 1.66 (1.31-2.10) | <0.001 | 1.69 (1.37-2.10) | <0.001 |
| 13 Non-esterified Fatty Acids | 0.82 (0.61-1.11) | 0.19 | 0.86 (0.65-1.14) | 0.28 |
| 14 Docosanoyl-carnitine | 0.71 (0.51-0.99) | 0.049 | 0.74 (0.53-1.01) | 0.06 |

*Adjusted for age, race, sex, hypertension, diabetes, hyperlipidemia, COPD, BMI, smoking and number of diseased coronary arteries. Death is from all causes, MACE is defined by myocardial infarction, coronary artery bypass grafting, or percutaneous coronary intervention occurring at least 7, 14, or 30 days after sample collection, respectively.
Abbreviations:
MACE indicates major adverse cardiac event;
HR, hazard ratio;
CI, confidence interval.

Peripheral blood metabolite profiles were independently associated with adverse outcomes in HFpEF, even after careful adjustment for clinical covariates. It was previously showed that elevated levels of medium-chain acylcarnitines and short-chain dicarboxylacylcarnitines were associated with increased risk of adverse outcomes in cardiovascular disease settings. These findings are now extended by demonstrating that these same metabolites, which are indicators of incomplete fatty acid ß-oxidation and endoplasmic reticulum stress, are markers of increased risk in HFpEF. This highlights the potential of metabolomic profiling for identifying high-risk HFpEF patients and may indicate new therapeutic targets.

***

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method for assessing risk of death or a major adverse cardiac event (MACE) in a subject diagnosed with heart failure with preserved ejection fraction (HFpEF), the method comprising: (a) determining in a sample from the subject the level of each metabolite in at least one factor, wherein the factor is selected from the group consisting of factor 1, factor 3, factor 4, factor 5, factor 10, factor 12, and factor 14; and (b) comparing the level of each metabolite in the sample to a standard, wherein the level of the metabolite in the subject relative to a standard is indicative of the risk of death or MACE in the subject, wherein factor 1 consists of medium-chain acylcarnitines, wherein factor 3 consists of short-chain dicarboxylacylcarnitines, wherein factor 4 consists of long-chain acylcarnitines, wherein factor 5 consists of ketone related metabolites, wherein factor 10 consists of glycine, ornithine, and tiglyl-carnitine, wherein factor 12 consists of 3-hydroxy-linoleyl-carnitine, and wherein factor 14 consists of docosanoyl-carnitine.

Clause 2. The method of clause 1, further comprising determining that the subject has a risk of death or MACE when the level of each metabolite in the subject is different from the standard.

Clause 3. A method for assessing risk of death or MACE in a subject diagnosed with HFpEF, the method comprising: (a) determining in a sample from the subject the level of each metabolite in at least one factor selected from the group consisting of factor 1, factor 3, factor 4, factor 5, factor 10, factor 12, and factor 14, wherein factor 1 consists of medium-chain acylcarnitines, wherein factor 3 consists of short-chain dicarboxylacylcarnitines, wherein factor 4 consists of long-chain acylcarnitines, wherein factor 5 consists of ketone related metabolites, wherein factor 10 consists of glycine, ornithine, and tiglyl-carnitine, wherein factor 12 consists of 3-hydroxy-linoleyl-carnitine, and wherein factor 14 consists of docosanoyl-carnitine; (b) calculating a weighted level of each metabolite by multiplying the determined level by a scoring coefficient specific for each metabolite; (c) adding the weighted level of each metabolite in the factor together to yield a factor score; (d) comparing the factor score of the sample to a non-HFpEF standard; and (e) determining that the subject has an increased risk of death or MACE when the factor score in the subject is different from the standard.

Clause 4. The method of clause 1 or 2 or 3, wherein factor 1 consists of medium-chain acylcarnitines selected from C8, C10, C12, C14:1, C14, C16:2, C16:1, C14:2, C12:1, and C10:1 acylcarnitines.

Clause 5. The method of clause 1 or 2 or 3, wherein factor 3 consists of short-chain dicarboxylacylcarnitines selected from C5-DC, C6:1-DC/C8:1-OH, C8:1-DC, C6-DC, Ci4-DC/C4-DC, C10-OH/C8-DC, and C12-OH/C10-DC acylcarnitines and the amino acid citrulline.

Clause 6. The method of clause 1 or 2 or 3, wherein factor 4 consists of long-chain acylcarnitine related metabolites selected from C18:1, C18:2, C18, C16, C20:4, and C16:1-OH/C14:1-DC acylcarnitines.

Clause 7. The method of clause 1 or 2 or 3, wherein factor 5 consists of ketone related metabolites selected from ketones, ß-hydroxybutyrate, ß-hydroxybutyryl-carnitine, acetylcarnitine, and alanine.

Clause 8. The method of any one of the preceding clauses, wherein the level of each metabolite in more than one factor is determined in step (a).

Clause 9. The method of any one of the preceding clauses, wherein the level of each metabolite in two factors is determined in step (a).

Clause 10. The method of any one of the preceding clauses, wherein the level of each metabolite in three factors is determined in step (a).

Clause 11. The method of any one of the preceding clauses, wherein the level of each metabolite in four factors is determined in step (a).

Clause 12. The method of any one of the preceding clauses, wherein the level of each metabolite in five factors is determined in step (a).

Clause 13. The method of any one of the preceding clauses, wherein the level of each metabolite in six factors is determined in step (a).

Clause 14. The method of any one of clauses 1-2 and 4-13, comprising determining the level of each metabolite in factor 1, wherein an increased level of the metabolite in the subject is indicative of the risk of death or MACE in the subject.

Clause 15. The method of any one of clauses 1-2 and 4-13, comprising determining the level of each metabolite in factor 3, wherein an increased level of the metabolite in the subject is indicative of the risk of death or MACE in the subject.

Clause 16. The method of any one of clauses 1-2 and 4-13, comprising determining the level of each metabolite in factor 4, wherein an increased level of the metabolite in the subject is indicative of the risk of death or MACE in the subject.

Clause 17. The method of any one of clauses 1-2 and 4-13, comprising determining the level of each metabolite in factor 5, wherein an increased level of the metabolite in the subject is indicative of the risk of death or MACE in the subject.

Clause 18. The method of any one of clauses 1-2 and 4-13, comprising determining the level of each metabolite in factor 12, wherein an increased level of the metabolite in the subject is indicative of the risk of death or MACE in the subject.

Clause 19. The method of any one of clauses 1-2 and 4-13, comprising determining the level of each metabolite in factor 10, wherein a decreased level of the metabolite in the subject is indicative of the risk of death or MACE in the subject.

Clause 20. The method of any one of clauses 1-2 and 4-13, comprising determining the level of each metabolite in factor 14, wherein a decreased level of the metabolite in the subject is indicative of the risk of death or MACE in the subject.

Clause 21. The method of any one of clauses 3-13, comprising determining the level of each metabolite in factor 1, wherein an increased level of the factor score for the subject is indicative of the risk of death or MACE in the subject.

Clause 22. The method of any one of clauses 3-13, comprising determining the level of each metabolite in factor 3, wherein an increased level of the factor score for the subject is indicative of the risk of death or MACE in the subject.

Clause 23. The method of any one of clauses 3-13, comprising determining the level of each metabolite in factor 4, wherein an increased level of the factor score for the subject is indicative of the risk of death or MACE in the subject.

Clause 24. The method of any one of clauses 3-13, comprising determining the level of each metabolite in factor 5, wherein an increased level of the factor score for the subject is indicative of the risk of death or MACE in the subject.

Clause 25. The method of any one of clauses 3-13, comprising determining the level of each metabolite in factor 12, wherein an increased level of the factor score for the subject is indicative of the risk of death or MACE in the subject.

Clause 26. The method of any one of clauses 3-13, comprising determining the level of each metabolite in factor 10, wherein a decreased level of the factor score for the subject is indicative of the risk of death or MACE in the subject.

Clause 27. The method of any one of clauses 3-13, comprising determining the level of each metabolite in factor 14, wherein a decreased level of the factor score for the subject is indicative of the risk of death or MACE in the subject.

Clause 28. A method of developing a treatment plan for a subject comprising steps (a) and (b) of clause 1, and further comprising (c) determining that the subject has a risk of death or MACE when the level of each metabolite in the subject is different from the standard; and (d) developing a treatment plan when the subject is determined in step (c) to have a risk of death or MACE.

Clause 29. The method of clause 28, wherein the treatment plan comprises at least one therapy selected from the group consisting of lifestyle modification, angiotensin converting enzyme inhibitors, angiotensin receptor blocker, beta blocker, aldosterone antagonist, hydralazine, nitrate, pacemaker, implantable cardiac defibrillator, and heart transplant, or a combination thereof.

Clause 30. A method for diagnosing heart failure with preserved ejection fraction (HFpEF) in a subject, the method comprising: (a) determining in a sample from the subject the level of each metabolite in factor 4; and (b) comparing the level of each metabolite in the sample to a standard, wherein the level of the metabolite in the subject relative to a standard is indicative of the subject having HFpEF, wherein factor 4 consists of long chain acylcarnitines.

Clause 31. The method of clause 30, wherein factor 4 consists of long-chain acylcarnitine related metabolites selected from C18:1, C18:2, C18, C16, C20:4, and C16:1-OH/C14:1-DC acylcarnitines.

Clause 32. The method of clause 30 or 31, further comprising identifying the subject as having HFpEF when the level of each metabolite in the subject is greater than the standard.

Clause 33. The method of any one of the preceding clauses, wherein the sample is blood.

Clause 34. The method of any one of the preceding clauses, wherein the level of the metabolite is detected using mass spectrometry.

Clause 35. The method of any one of the preceding clauses, wherein the level of the metabolite is detected using a colorimetric or fluorometric assay.

The invention claimed is:

1. A method for treating a subject diagnosed with heart failure with preserved ejection fraction (HFpEF) and having an increased risk of death or a major adverse cardiac event (MACE), the method comprising:
   (a) determining in a sample from the subject the level of each metabolite in at least one factor, the determined level being different from the level of the metabolite in a standard sample, wherein the factor is selected from factor 1, factor 3, factor 4, factor 5, factor 10, factor 12, and factor 14,
   wherein factor 1 consists of medium-chain acylcarnitines,
   wherein factor 3 consists of short-chain dicarboxylacyl-carnitines,
   wherein factor 4 consists of long-chain acylcarnitines,
   wherein factor 5 consists of ketone related metabolites,
   wherein factor 10 consists of glycine, ornithine, and tiglyl-carnitine,
   wherein factor 12 consists of 3-hydroxy-linoleyl-carnitine, and
   wherein factor 14 consists of docosanoyl-carnitine;
   (b) determining that the subject has an increased risk of death or MACE based on the determined level of each metabolite in the subject in step (a): and
   (c) administering to the subject a treatment for heart failure comprising at least one therapy selected from angiotensin converting enzyme inhibitor, angiotensin receptor blocker, beta blocker, aldosterone antagonist, hydralazine, nitrate, pacemaker, implantable cardiac defibrillator, heart transplant, or a combination thereof.

2. A method for treating a subject diagnosed with HFpEF and having an increased risk of death or MACE, the method comprising:
   (a) determining in a sample from the subject the level of each metabolite in at least one factor selected from factor 1, factor 3, factor 4, factor 5, factor 10, factor 12, and factor 14,
   wherein factor 1 consists of medium-chain acylcarnitines,
   wherein factor 3 consists of short-chain dicarboxylacyl-carnitines, wherein factor 4 consists of long-chain acylcarnitines,
   wherein factor 5 consists of ketone related metabolites,
   wherein factor 10 consists of glycine, ornithine, and tiglyl-carnitine,
   wherein factor 12 consists of 3-hydroxy-linoleyl-carnitine,
   wherein factor 14 consists of docosanoyl-carnitine,
   wherein the determined level of each metabolite multiplied by a scoring coefficient specific for each metabolite determines a weighted level of each metabolite, and wherein the weighted level of each metabolite in the factor added together yields a factor score in the subject that is different from the factor score of a non-HFpEF standard;
   (b) determining that the subject has an increased risk of death or MACE based on the factor score in the subject determined in step (a); and
   (c) administering to the subject a treatment for heart failure comprising at least one therapy selected from angiotensin converting enzyme inhibitor, angiotensin receptor blocker, beta blocker, aldosterone antagonist, hydralazine, nitrate, pacemaker, implantable cardiac defibrillator, heart transplant, or a combination thereof.

3. The method of claim 1, wherein factor 1 consists of medium-chain acylcarnitines selected from C8, C10, C12, C14:1, C14, C16:2, C16:1, C14:2, C12:1, and C10:1 acylcarnitines,
   wherein factor 3 consists of short-chain dicarboxylacyl-carnitines selected from C5-DC, C6:1-DC/C8:1-OH, C8:1-DC, C6-DC, Ci4-DC/C4-DC, C10-OH/C8-DC, and C12-OH/C10-DC acylcarnitines and the amino acid citrulline,
   wherein factor 4 consists of long-chain acylcarnitine related metabolites selected from C18:1, C18:2, C18, C16, C20:4, and C16:1-OH/C14:1-DC acylcarnitines, and
   wherein factor 5 consists of ketone related metabolites selected from ketones, ß-hydroxybutyrate, ß-hydroxybutyryl-carnitine, acetylcarnitine, and alanine.

4. The method of claim 1, wherein the level of each metabolite in more than one factor is determined in step (a).

5. The method of claim 1, wherein the level of each metabolite in two factors is determined in step (a).

6. The method of claim 1, wherein the level of each metabolite in three factors is determined in step (a).

7. The method of claim 1, wherein the level of each metabolite in four factors is determined in step (a).

8. The method of claim 1, wherein the level of each metabolite in five factors is determined in step (a).

9. The method of claim 1, wherein the level of each metabolite in six factors is determined in step (a).

10. The method of claim 1, wherein the factor is selected from factor 1, factor 3, factor 4, factor 5, and factor 12, and wherein the determined level of each metabolite in the selected factor in the subject is greater than the level of the metabolite in a standard sample.

11. The method of claim 1, wherein the factor is selected from factor 10 and factor 14, and wherein the determined level of each metabolite in the selected factor in the subject is less than the level of the metabolite in a standard sample.

12. The method of claim 2, wherein the factor is selected from factor 1, factor 3, factor 4, factor 5, and factor 12, and wherein the factor score for the subject is greater than the factor score of a non-HFpEF standard.

13. The method of claim 2, wherein the factor is selected from factor 10and factor 14, and wherein the factor score for the subject is less than the factor score of a non-HFpEF standard.

14. A method for treating heart failure with preserved ejection fraction (HFpEF) in a subject, the method comprising:
   (a) determining in a sample from the subject the level of each metabolite in factor 4 that is greater than to the level in a standard sample, wherein factor 4 consists of long chain acylcarnitines;
   (b) diagnosing the subject as having HFpEF based on the determined level of each metabolite in the subject in step (a) and
   (c) administering to the subject a treatment for heart failure comprising at least one therapy selected from angiotensin converting enzyme inhibitor, angiotensin receptor blocker, beta blocker, aldosterone antagonist, hydralazine, nitrate, pacemaker, implantable cardiac defibrillator, heart transplant, or a combination thereof.

15. The method of claim 14, wherein factor 4 consists of long chain acylcarnitines selected from C18:1, C18:2, C18, C16, C20:4, and C16:1-OH/C14:1-DC acylcarnitines.

16. The method of claim 1, wherein the sample is blood.

17. The method of claim 1, wherein the level of the metabolite is detected using mass spectrometry, or a colorimetric assay, or fluorometric assay.

* * * * *